United States Patent
Liang et al.

(10) Patent No.: US 11,612,603 B1
(45) Date of Patent: Mar. 28, 2023

(54) 3-TRIAZOLYL METHYL-1,3,5-TRIAZINE-2,4-DIONE COMPOUNDS AND PREPARATION METHOD AND APPLICATION THEREOF

(71) Applicant: SHAANXI PANLONG PHARMACEUTICAL CO., LTD., Xi'an (CN)

(72) Inventors: Chengyuan Liang, Xi'an (CN); Liang Xin, Xi'an (CN); Lei Tian, Xi'an (CN); Jingyi Li, Xi'an (CN); Xiaolin Xie, Xi'an (CN); Dezhu Zhang, Xi'an (CN); Kangxiong Wu, Xi'an (CN); Shaojun Zhang, Xi'an (CN); Xiuding Yang, Xi'an (CN); Sundian Liu, Xi'an (CN); Yuting Liu, Xi'an (CN); Zhao Ma, Xi'an (CN); Xuhua Zhou, Xi'an (CN)

(73) Assignee: SHAANXI PANLONG PHARMACEUTICAL CO., LTD., Shaanxi (CN)

( * ) Notice: Subject to any disclaimer, the term of this patent is extended or adjusted under 35 U.S.C. 154(b) by 0 days.

(21) Appl. No.: 17/866,514

(22) Filed: Jul. 17, 2022

(30) Foreign Application Priority Data

Jun. 1, 2022 (CN) .......................... 202210618258.2

(51) Int. Cl.
*A61K 31/53* (2006.01)
*A61P 31/14* (2006.01)

(52) U.S. Cl.
CPC .............. *A61K 31/53* (2013.01); *A61P 31/14* (2018.01)

(58) Field of Classification Search
None
See application file for complete search history.

*Primary Examiner* — Leslie A. Royds Draper

(57) ABSTRACT

Disclosed is a compound of formula I, a pharmaceutically acceptable salt, or a tautomer thereof.

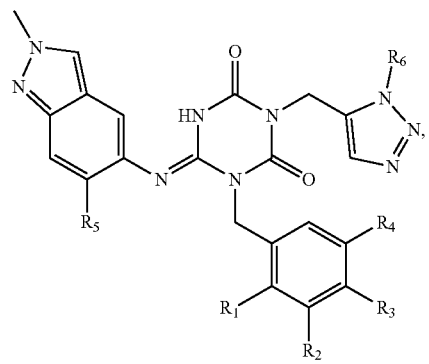

formula I. $R_1$, $R_2$, $R_3$ and $R_4$ are independently selected from the group consisting of hydrogen, methyl group, tert-butyl group, methoxy group, difluoromethyl, trifluoromethyl, trifluoromethoxy, nitro, halogen, phenyl and aromatic heterocyclic; $R_5$ is a hydrogen or halogen; and $R_6$ is hydrogen, C1-4 alkane or C1-4 cycloalkane.

2 Claims, No Drawings

3-TRIAZOLYL METHYL-1,3,5-TRIAZINE-2,4-DIONE COMPOUNDS AND PREPARATION METHOD AND APPLICATION THEREOF

The present application claims priority to Chinese Patent Application No. 202210618258.2, filed on Jun. 1, 2022, which is incorporated by reference for all purposes as if fully set forth herein.

TECHNICAL FIELD

The invention belongs to the technical field of medicinal chemistry, and in particular relates to 3-triazolyl methyl-1, 3,5-triazine-2,4-dione compounds and preparation method and application thereof.

BACKGROUND TECHNIQUE

COVID-19 (new coronavirus pneumonia) is highly contagious and highly pathogenic, and its mutant strains Delta and Omicron have stronger transmission ability. The endless mutant strains make the global epidemic situation more complicated. The novel coronavirus has posed a serious threat to human health, social stability and economic development.

$3CL^{pro}$ (3C-like protease, also known as major protease $M^{pro}$), as an important non-structural protein in coronaviruses, has a cleavage site similar to the 3C protease of microRNA virus, and plays an important role in the replication and transcription of progeny viruses. $3CL^{pro}$ has three domains. Domains I and 11 are mainly composed of 3-sheet structure, and domain III is mainly composed of α-helix structure. The active site is located in the groove formed between domains I and II. Domain III is involved in dimer formation. Compared with domain III, the sequence conservation of domain I and domain II of different coronaviruses is higher, which is consistent with their active sites being located in the first two domains. $3CL^{pro}$ uses conservative cysteine and histidine as catalytic amino acids to form a catalytic duplex, in which cysteine is a nucleophilic attack group and histidine is a basic group. Coronavirus $3CL^{pro}$ is essential for viral replication and highly conserved, making it an ideal anti-coronavirus drug target.

SUMMARY OF THE INVENTION

In one embodiment, the present application discloses a compound of formula I, a pharmaceutically acceptable salt, a diastereomer, or a tautomer thereof:

formula I

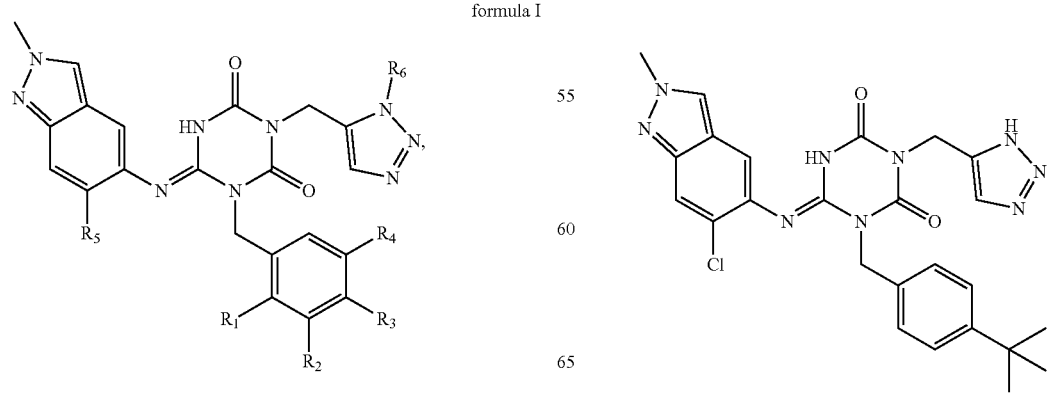

$R_1$, $R_2$, $R_3$ and $R_4$ are independently selected from the group consisting of hydrogen, methyl group, tert-butyl group, methoxy group, difluoromethyl, trifluoromethyl, trifluoromethoxy, nitro, halogen, phenyl and aromatic heterocyclic; $R_5$ is a hydrogen or halogen; and $R_6$ is hydrogen, C1-4 alkane or C1-4 cycloalkane.

In another embodiment, the compound is selected from the group consisting of:

1

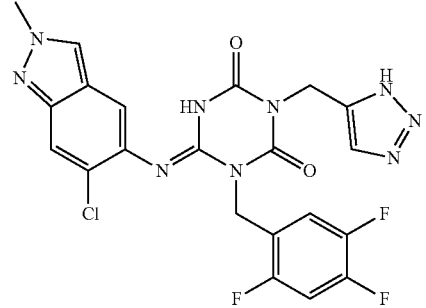

2

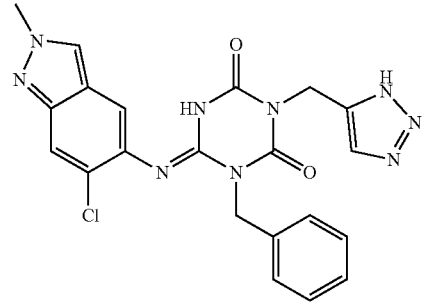

3

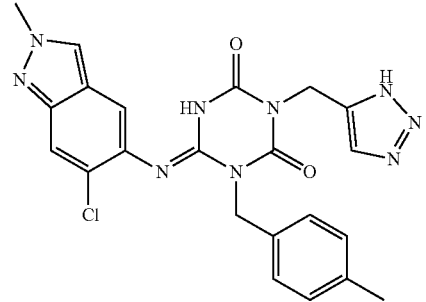

4

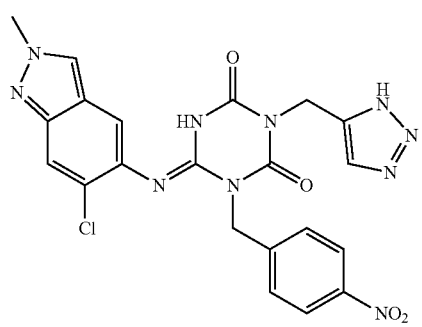
5
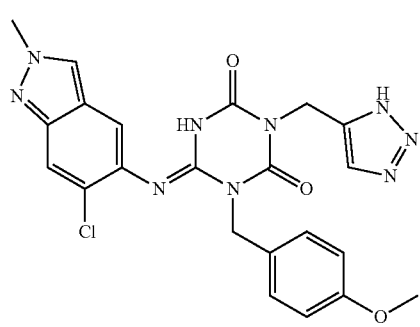
6
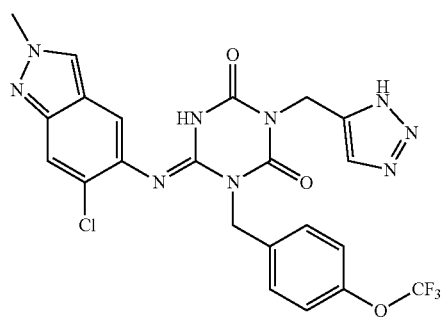
7
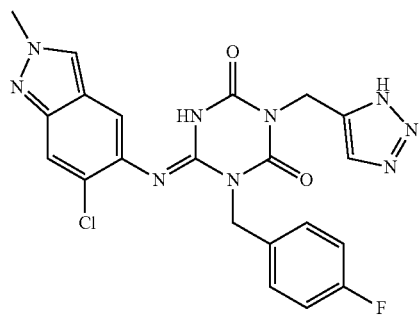
8
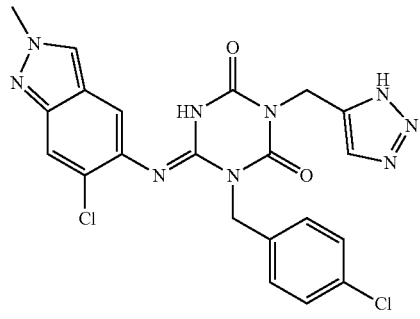
9
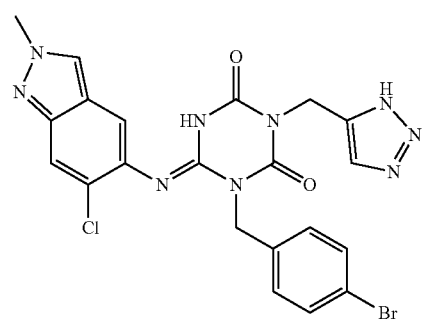
10
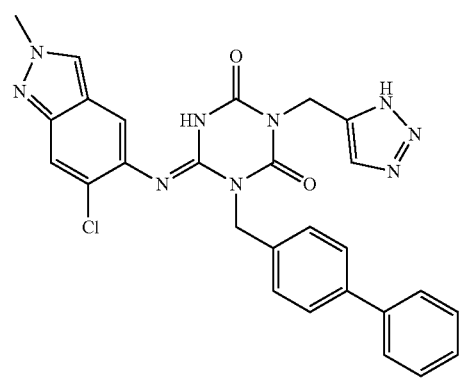
11
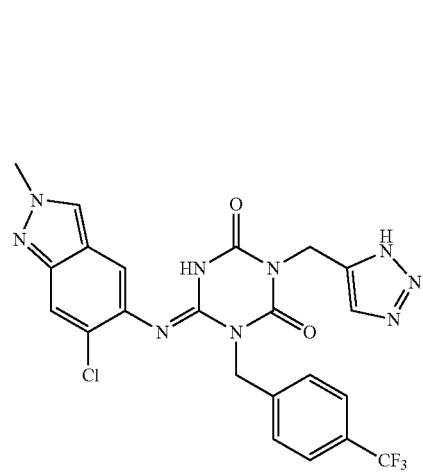
12
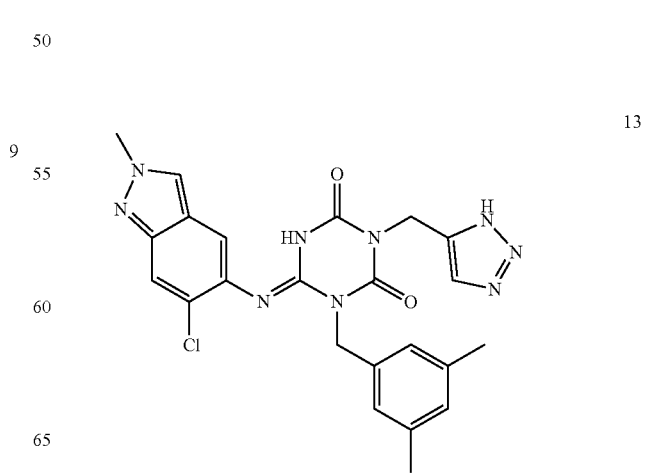
13

14
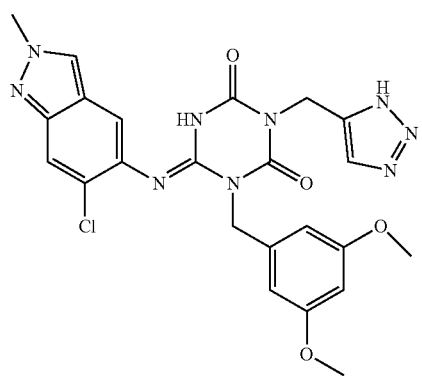
15
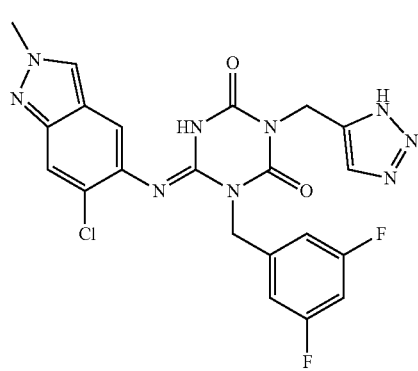
16
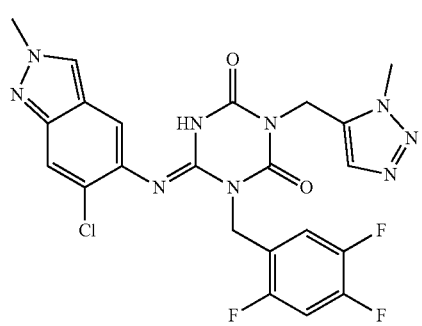
17
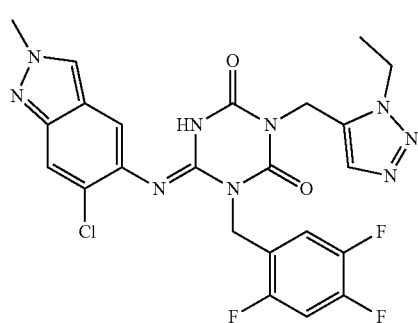
18
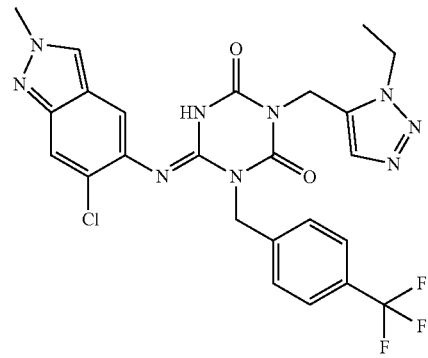
19
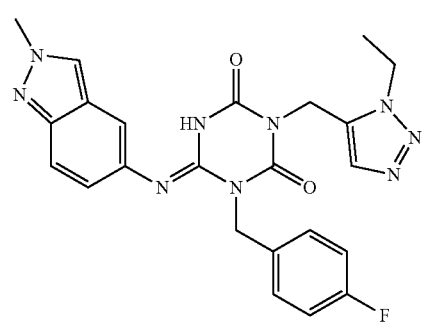
20
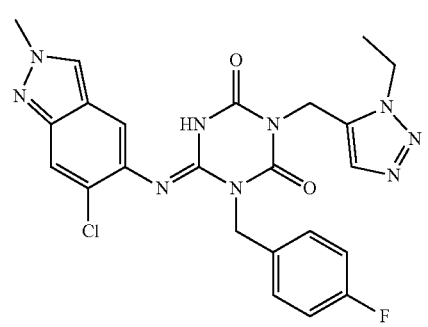
21
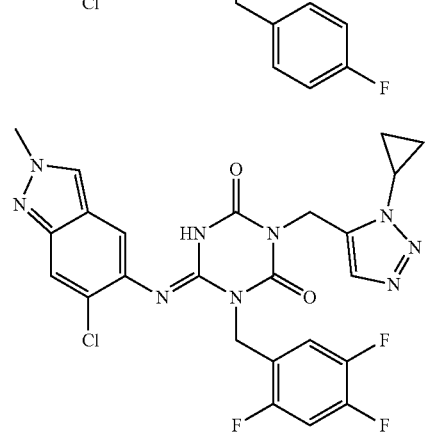
22
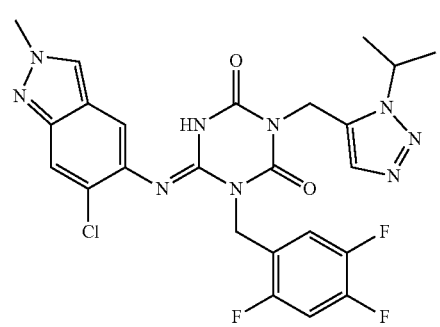

-continued

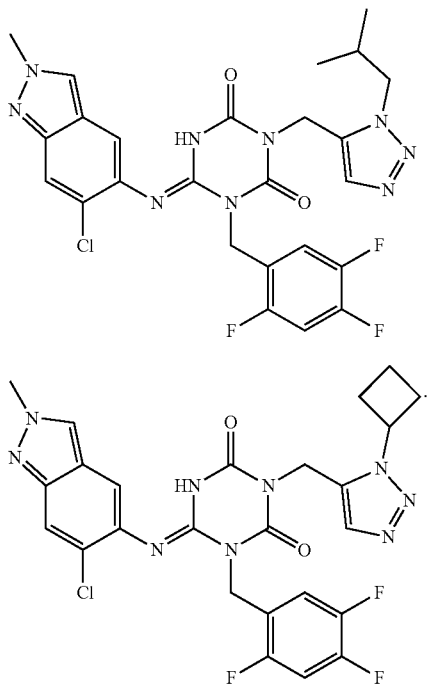

In another embodiment, the pharmaceutically acceptable salt includes one selected from the group consisting of hydrochloric acid, hydrobromic acid, sulfuric acid, nitric acid, phosphoric acid, acetic acid, fumaric acid, maleic acid, oxalic acid, malonic acid, succinic acid, citric acid, malic acid, methanesulfonic acid, ethanesulfonic acid, benzenesulfonic acid, toluenesulfonic acid, glutamic acid, and aspartic acid.

In another embodiment, the present application discloses an anti-coronavirus pharmaceutical preparation including the compound of present application.

In another embodiment, the coronavirus is novel coronavirus SARS-CoV-2.

Compared with the prior art, the present invention has the following beneficial effects:

The the $3CL^{pro}$ inhibitory activity test results show that the compounds of the present invention have a strong effect on $3CL^{pro}$ Inhibitory effect. Specifically, the $IC_{50}$ values of compounds 1, 7, 12, 15, 16, 17, 18, 22 and 23 against $3CL^{pro}$ are all below 200 nM, among which, compared with the new coronavirus drugs S-216722 and PF-07321332, Compound 1 has the best inhibitory activity ($IC_{50}$<100 nM); $3CL^{pro}$ cytotoxicity test results show that the inhibitory rate of compound 1 on A549 cells, HepG2 cells and HEK293 cells is lower than that of PF-07321332 and S-217622 at any concentration, which is less toxic than the two positive drugs, and can be developed and applied as an anti-coronavirus drug.

The invention provides a preparation method of 3-triazolylmethyl-1,3,5-triazine-2,4-dione compounds. The method can be carried out under relatively mild conditions, with low requirements for reaction equipment and low environmental pollution; at the same time, the atom economy is high, suitable for industrial production.

DETAILED DESCRIPTION

In order to make those skilled in the art better understand the solutions of the present invention, the technical solutions in the embodiments of the present invention will be clearly and completely described below with reference to the accompanying drawings in the embodiments of the present invention. Obviously, the described embodiments are only Embodiments are part of the present invention, but not all of the embodiments. Based on the embodiments of the present invention, all other embodiments obtained by persons of ordinary skill in the art without creative efforts shall fall within the protection scope of the present invention.

It should be noted that the terms "first," "second" and the like in the description and claims of the present invention and the above drawings are used to distinguish similar objects, and are not necessarily used to describe a specific sequence or sequence. It is to be understood that the data so used may be interchanged under appropriate circumstances such that the embodiments of the invention described herein can be practiced in sequences other than those illustrated or described herein. Furthermore, the terms "comprising" and "having," and any variations thereof, are intended to cover non-exclusive inclusion, for example, a process, method, system, product or device comprising a series of steps or units is not necessarily limited to those expressly listed Rather, those steps or units may include other steps or units not expressly listed or inherent to these processes, methods, products or devices.

Below in conjunction with accompanying drawing, the present invention is described in further detail:

The present application discloses a compound of formula I, a pharmaceutically acceptable salt, a diastereomer, or a tautomer thereof:

formula I

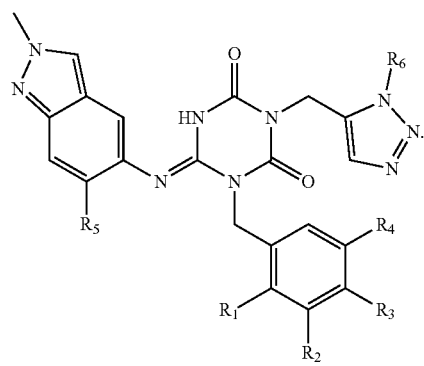

$R_1$, $R_2$, $R_3$ and $R_4$ are independently selected from the group consisting of hydrogen, methyl group, tert-butyl group, methoxy group, difluoromethyl, trifluoromethyl, trifluoromethoxy, nitro, halogen, phenyl and aromatic heterocyclic; $R_5$ is a hydrogen or halogen; and $R_6$ is hydrogen, C1-4 alkane or C1-4 cycloalkane.

The term "halogen" means fluorine, chlorine, bromine, and iodine.

The pharmaceutically acceptable salt can be a salt of hydrochloric acid, hydrobromic acid, sulfuric acid, nitric acid, phosphoric acid, acetic acid, fumaric acid, maleic acid, oxalic acid, malonic acid, succinic acid, lemon. acid, malic acid, methanesulfonic acid, ethanesulfonic acid, benzenesulfonic acid, toluenesulfonic acid, glutamic acid or aspartic acid.

The preparation method of the 3-triazolylmethyl-1,3,5-triazine-2,4-dione compound of the present invention is as follows.

(1) Alkylation 3-tert-butyl-6-(ethylthio)-1,3,5-triazine-2,4 (1H,3H)-dione (starting material) with bromobenzyl compounds to obtain compounds a1-a24.

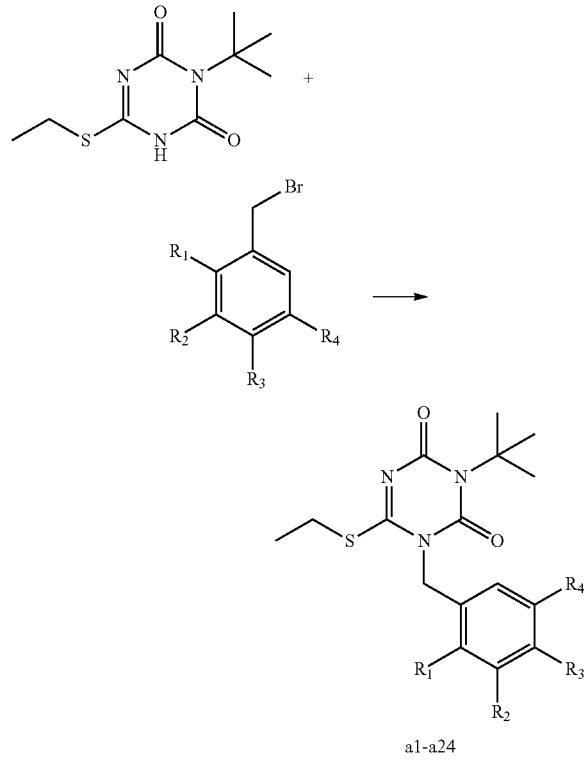

a1-a24

A molar ratio of 3-tert-butyl-6-(ethylthio)-1,3,5-triazine-2,4(1H,3H)-dione to bromobenzyl compounds is 1:1. The solvent used in the synthetic process of a1-a24 is acetonitrile. The reaction is carried is heating and refluxing conditions with potassium carbonate. The bromobenzyl compounds are:

| $R_1 =$ | $R_2 =$ | $R_3 =$ | $R_4 =$ | Structure |
|---|---|---|---|---|
| —F | —H | —F | —F | Br, 2,4,5-trifluorobenzyl |
| —H | —H | —H | —H | Br, benzyl |
| —H | —H | —CH$_3$ | —H | Br, 4-methylbenzyl |
| —H | —H | —C(CH$_3$) | —H | Br, 4-tert-butylbenzyl |
| —H | —H | —NO$_2$ | —H | Br, 4-nitrobenzyl |
| —H | —H | —OCH$_3$ | —H | Br, 4-methoxybenzyl |
| —H | —H | —OCF$_3$ | —H | Br, 4-trifluoromethoxybenzyl |
| —H | —H | —F | —H | Br, 4-fluorobenzyl |
| —H | —H | —Cl | —H | Br, 4-chlorobenzyl |
| —H | —H | —Br | —H | Br, 4-bromobenzyl |
| —H | —H | —Ph | —H | Br, 4-phenylbenzyl |
| —H | —H | —CF$_3$ | —H | Br, 4-trifluoromethylbenzyl |

| $R_1 =$ | $R_2 =$ | $R_3 =$ | $R_4 =$ | Structure |
|---|---|---|---|---|
| —H | —CH$_3$ | —H | —CH$_3$ | 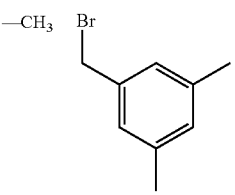 |
| —H | —OCH$_3$ | —H | —OCH$_3$ | 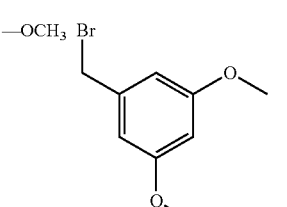 |
| —H | —F | —H | —F | 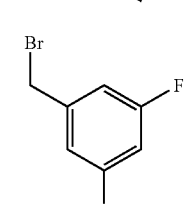 |

(2) Removing the tert-butyl group from the compound a1-a24 obtained in step (1) to obtain the corresponding compounds b1-b24, and then reacting with 3-bromopropyne to obtain the corresponding compounds c1-c24.

The preparation method of the compounds of the present application is as follows:

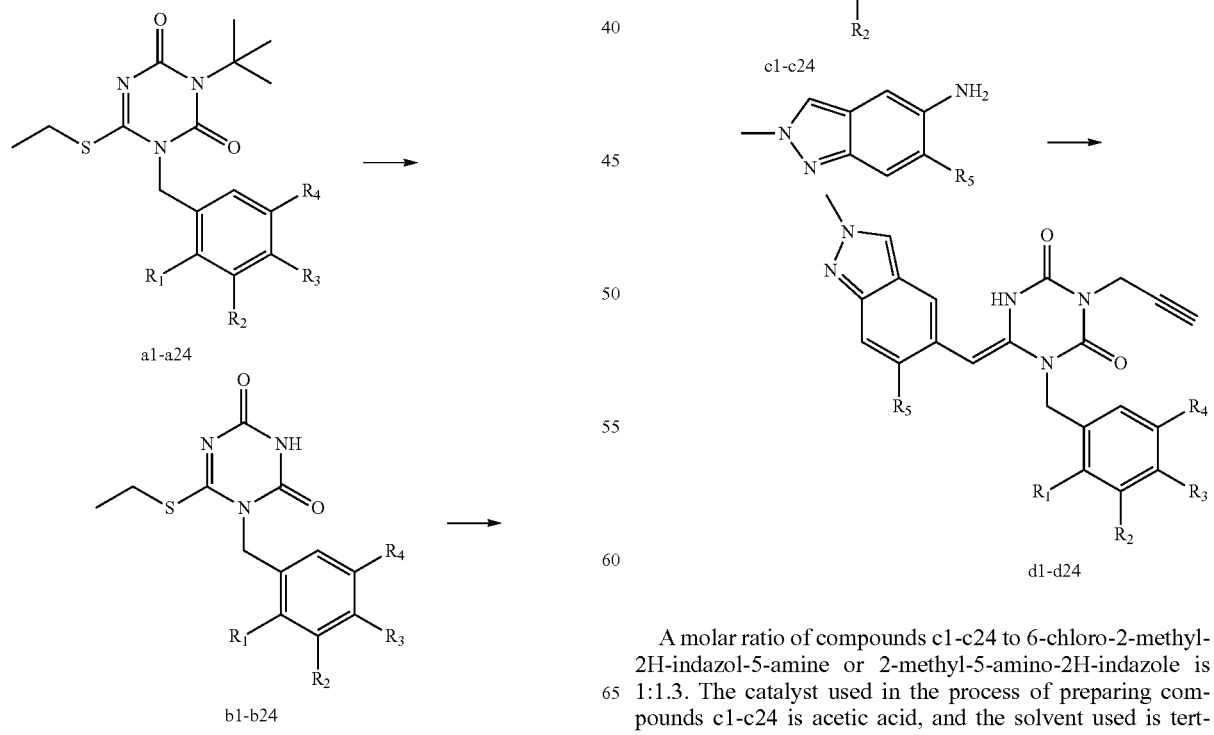

The solvent used in the synthesis process of compound b1-b24 is trifluoroacetic acid; a molar ratio of compounds b1-b24 to 3-bromopropyne is 1:1.2; the solvent used in the synthesis process of compounds c1-c24 is acetonitrile, and reaction is carried under heating and refluxing conditions with with potassium carbonate.

(3) The compounds c1-c24 obtained in step (2) react with 6-chloro-2-methyl-2H-indazol-5-amine or 2-methyl-5-amino-2H-indazole to obtain the corresponding compounds d1-d24;

A molar ratio of compounds c1-c24 to 6-chloro-2-methyl-2H-indazol-5-amine or 2-methyl-5-amino-2H-indazole is 1:1.3. The catalyst used in the process of preparing compounds c1-c24 is acetic acid, and the solvent used is tert-butanol.

(4) The compounds d1-d15 obtained in step (3) react with azidotrimethylsilane to obtain 3-triazolylmethyl-1,3,5-triazine-2,4-diones 1-15 (formula I, $R_6$ is H); or The compounds d16-d20 prepared in step (3) react with azidotrimethylsilane to obtain the corresponding compounds e16-e20, which further react with methyl trifluoromethanesulfonate or ethyl trifluoromethanesulfonate to obtain 3-triazolylmethyl-1,3,5-triazine-2,4-diones 16-20 (formula I, $R_6$ is C1-2 alkane); or The compounds d21-d24 obtained in step (3) react with azidoalkane compounds to obtain 3-triazolylmethyl-1,3,5-triazine-2,4-diones 21-24 (formula I, $R_6$ is C3-4 alkane or cycloalkane)

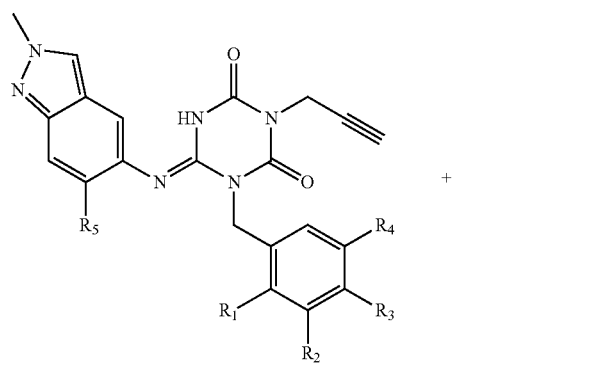

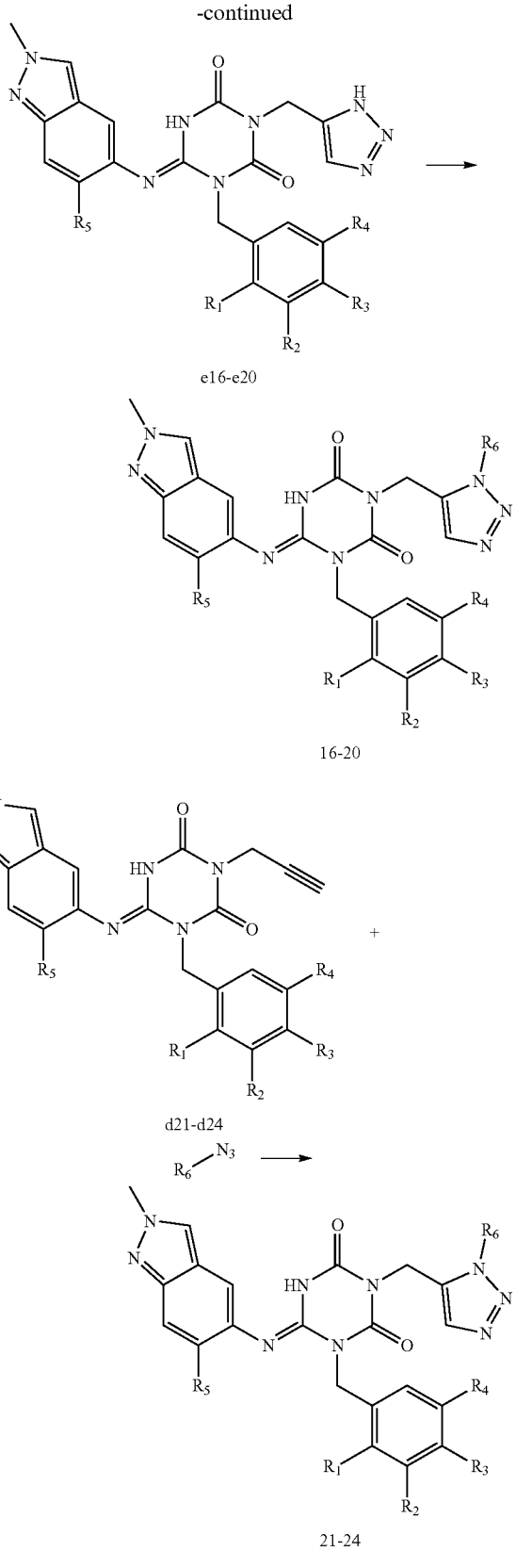

A molar ratio of compounds d1-d20 to azidotrimethylsilane is 1:1.5; a molar ratio of methyl trifluoromethanesulfonate or ethyl trifluoromethanesulfonate to compounds e16-e20 is 1:1.2; a molar ratio of compounds d21-d24 to azidoalkane compounds is 1:1.2. The solvents used in the synthesis process of compounds 1-15 are N,N-dimethylformamide and methanol, and the catalyst used is cuprous iodide. The solvent used in the synthesis process of compounds 16-20 is 1,4-dioxane, and the catalyst used is bis-dibenzylideneacetone palladium, 2-(di-tert-butylphosphine)-3,6-dimethoxy-2'-4'-6'tri-1-propyl-1,1'-bisphenyl and potassium phosphate.

The solvents used in the synthesis of compounds 21-24 are N,N-dimethylformamide, tetrahydrofuran and water, and the catalysts used are copper sulfate pentahydrate and sodium ascorbate.

Examples of the synthesis of the above compounds are given below.

1. Preparation of Compounds 1-24

Example 1

Compound 1: Preparation of (E)-3-(1H-1,2,3-triazol-5-yl)methyl)-6-(6-chloro-2-methyl-2H-indazol-5-yl)imino)-1-(2,4,5-trifluorobenzyl)-1,3,5-triazine-2,4-dione (1) Preparation of Compound a1

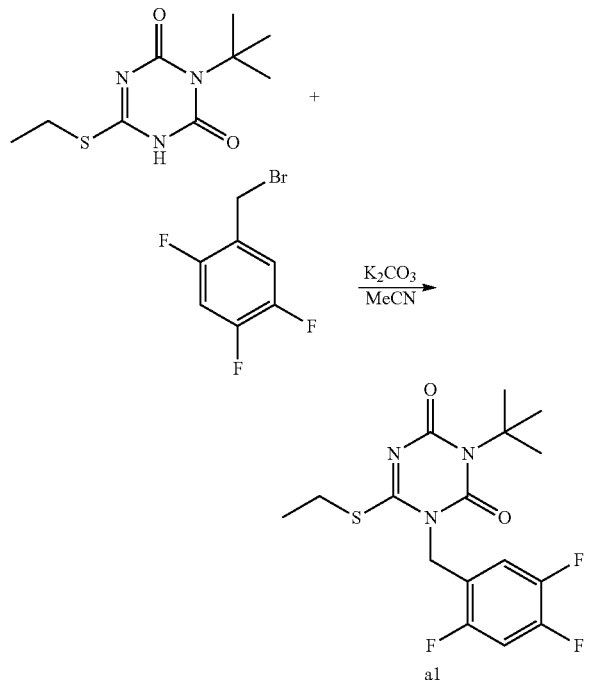

3-tert-Butyl-6-(ethylthio)-1,3,5-triazine-2,4(1H,3H)-dione (114.7 mg, 0.5 mmol), 2,4,5-triazine fluorobenzyl bromide (112.5 mg, 0.5 mmol) and potassium carbonate (82.9 mg, 0.6 mmol) were placed in the reactor, dissolved in 10 mL of acetonitrile, heated to reflux, stirred for 3 hours, and monitored by TLC. After the reaction was complete, the reaction mixture was concentrated under reduced pressure to remove the solvent. The solid residue obtained was washed with saturated aqueous sodium chloride solution, extracted with ethyl acetate. The organic phase was collected, separated and purified by column chromatography (petroleum ether:ethyl acetate (V:V)=3:1 as mobile phase) and dried to obtain 168.9 mg of compound a1, a yield of 90.47%. $^1$HNMR spectrum confirmed the structure of compound a1.

(2) Preparation of Compound c1

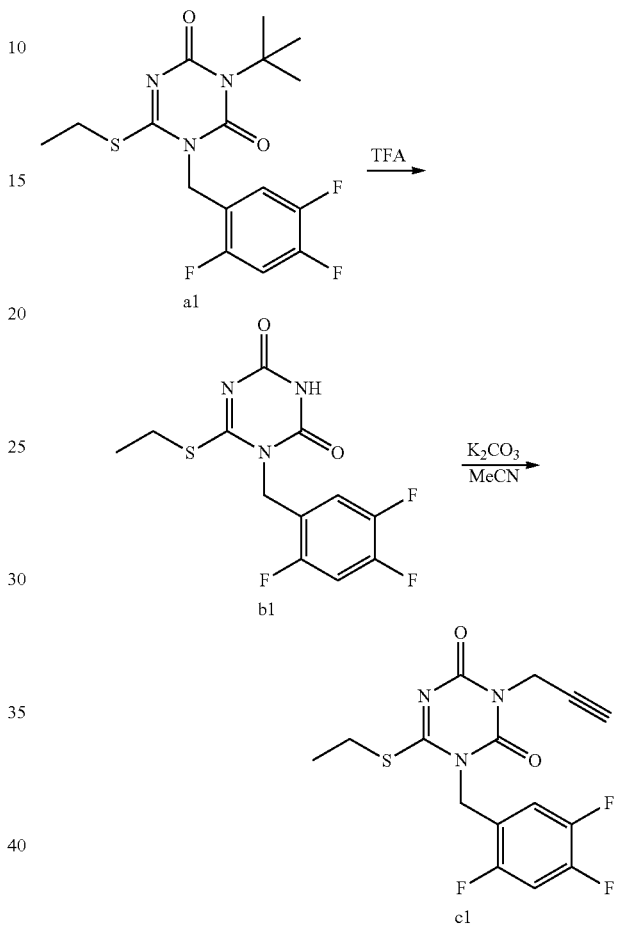

Step 1: Synthesis of Compound b1

The obtained compound a1 (373.4 mg, 1 mmol) was placed in a reactor, 5 mL of trifluoroacetic acid (TFA) was added, stirred at room temperature overnight, then azeotropically concentrated with toluene to remove the solvent, and dried to obtain 298.6 mg of compound b1, a yield of 94.10%.

Step 2: Synthesis of Compound c1

Compound b1 (317.3 mg, 1 mmol), 3-bromopropyne (0.1 mL, 1.2 mmol) and potassium carbonate (165.9 mg, 1.2 mmol) were placed in a reactor, dissolved in 10 mL of acetonitrile, heated to reflux and stirred. The reaction was carried out for 5 hours and monitored by TLC.

After the reaction was complete, the obtained reaction solution was washed with saturated aqueous sodium chloride solution, extracted with ethyl acetate, the organic phase was collected, separated and purified by column chromatography (petroleum ether:ethyl acetate (V:V)=1:1 as mobile phase). After drying, 279.9 mg of compound c1 was (3) Preparation of Compound d1

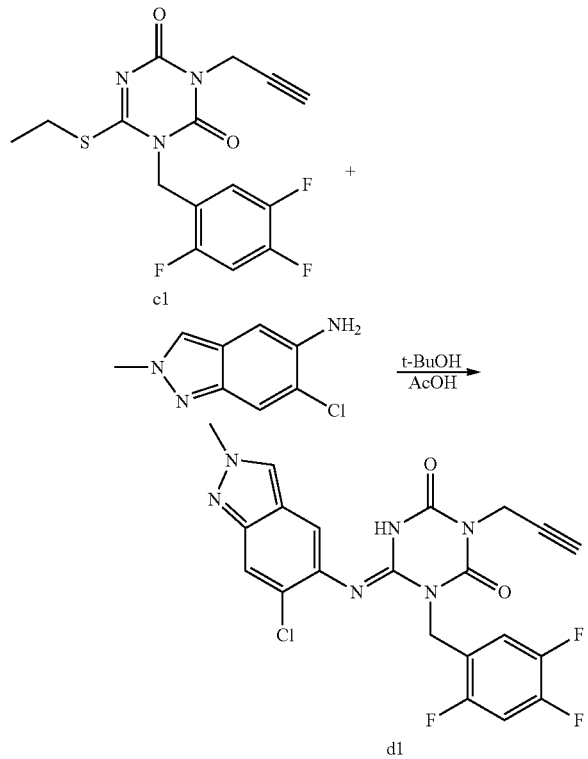

Compound c1 (177.7 mg, 0.5 mmol) and 6-chloro-2-methyl-2H-indazol-5-amine (118.1 mg, 0.65 mmol) and acetic acid (570 μL, 10 mmol) were placed in a reactor, 5 mL of tert-butanol was added, and the reaction was stirred at 100° C. for 4 hours and monitored by TLC. After the reaction was completed, the reaction mixture was cooled to room temperature, concentrated under reduced pressure, separated and purified by column chromatography (cyclohexane:ethyl acetate (V:V)=10:1 as mobile phase), and dried to obtain 125.6 mg of compound d1, a yield of 52.90%. $^1$HNMR spectrum confirmed the structure of compound d1.

(4) Preparation of Compound 1

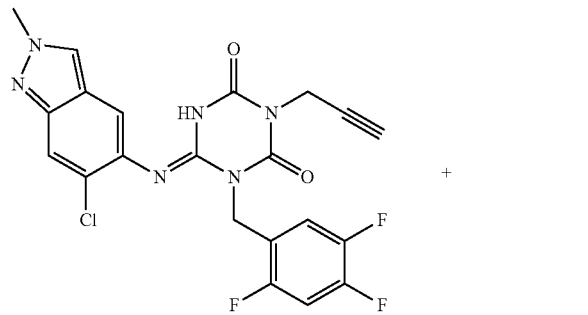

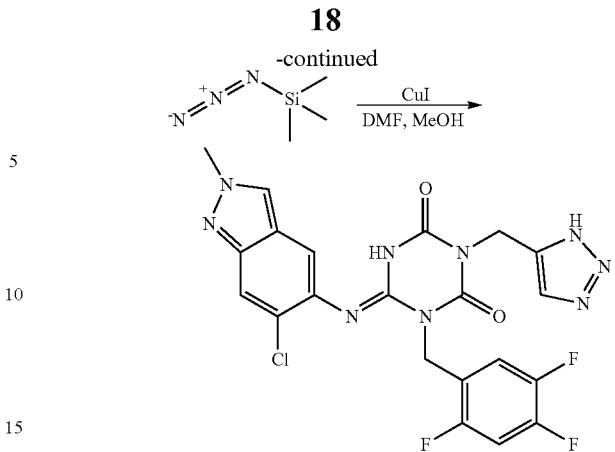

Compound d1 (2.4 g, 5 mmol), azidotrimethylsilane (864.1 mg, 7.5 mmol) and cuprous iodide (47.6 mg, 0.25 mmol) were placed in a reactor with a mixture of 90 mL N,N-dimethylformamide and 10 mL of methanol, and the reaction was heated and stirred overnight, and monitored by TLC. After the reaction was completed, it was cooled to room temperature. The obtained reaction solution was washed with saturated aqueous sodium chloride solution, extracted with ethyl acetate, the organic phase was collected, separated and purified by column chromatography (dichloromethane:methanol (V:V)=12:1 as mobile phase), and dried to obtain 995.3 mg of compound 1, a yield of 38.44%.

$^1$H NMR (600 MHz, DMSO) δ 14.88-14.53 (m, 1H), 10.99 (s, 1H), 8.23 (s, 1H), 7.83-7.50 (m, 4H), 7.12 (s, 1H), 5.23 (d, J=54.0 Hz, 2H), 4.99 (s, 2H), 4.16 (d, J=31.9 Hz, 3H).

$^{13}$C NMR (151 MHz, DMSO) δ 154.87, 153.65, 151.31, 150.18, 148.58, 146.61, 145.89, 139.91, 137.12, 132.97, 127.63, 126.37, 124.56, 122.26, 121.66, 117.32, 111.72, 106.19, 55.38, 37.21, 31.15.

Example 2

Compound 2: Preparation of (E)-3-((1H-1,2,3-triazol-5-yl)methyl)-1-benzyl-6-((6-chloro-2-methyl-2H-indazole-5)-yl)imino)-1,3,5-triazine-2,4-dione

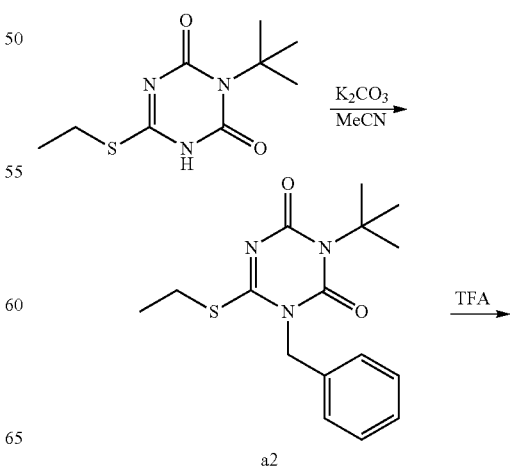

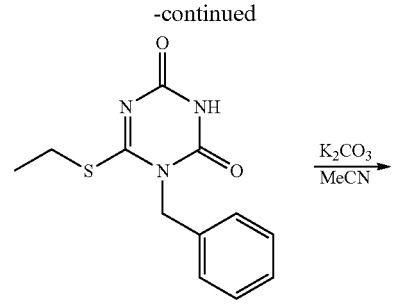
b2
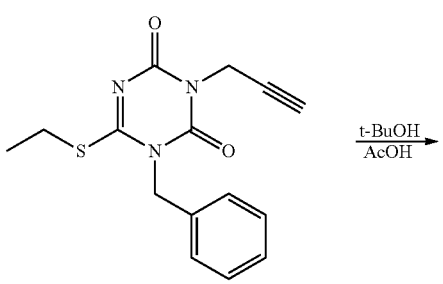
c2
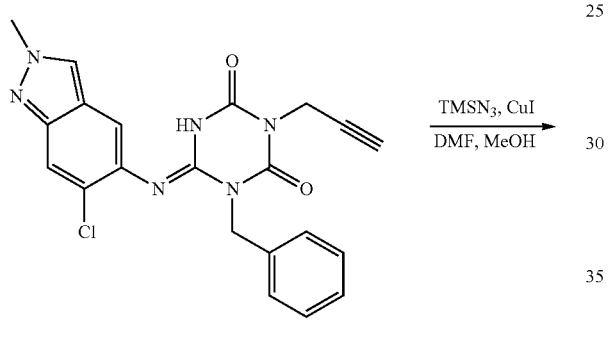
d2
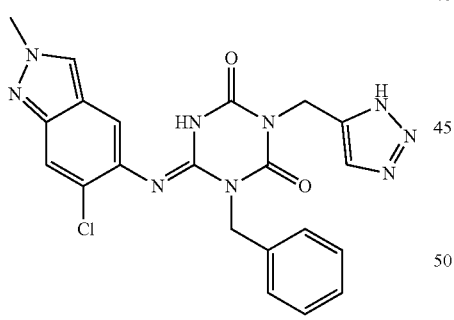
2
Compound 2 was prepared in the same way as Compound 1 (Example 1) with different starting materials, a yield of 42.23%.
$^1$H NMR (600 MHz, DMSO) δ 14.91-14.49 (m, 1H), 11.02 (s, 1H), 8.84 (s, 2H), 8.05-7.92 (m, 2H), 7.86-7.51 (m, 4H), 7.10 (s, 1H), 5.25 (d, J=53.2 Hz, 2H), 5.12 (s, 2H), 4.11 (d, J=31.6 Hz, 3H).
$^{13}$C NMR (151 MHz, DMSO) δ 147.66, 146.32, 143.23, 140.09, 138.21, 136.11, 135.78, 129.85, 127.56, 122.56, 122.12, 112.25, 111.12, 107.56, 107.45, 106.01, 105.56, 35.12, 34.07.
Example 3
Compound 3: Preparation of (E)-3-(1H-1,2,3-triazol-5-yl)methyl)-6-(6-chloro-2-methyl-2H-indazol-5-yl)imino)-1-(4-methylbenzyl)-1,3,5-triazine-2,4-dione
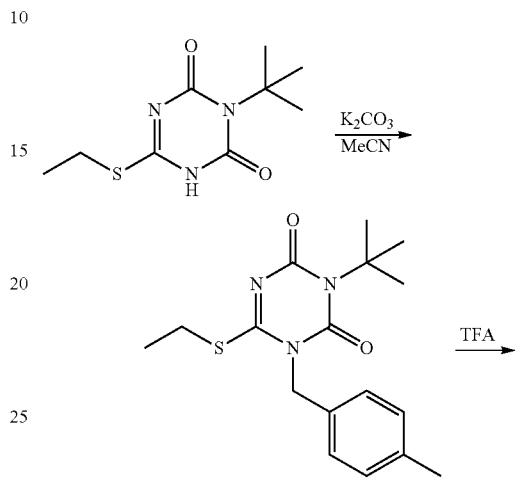
a3
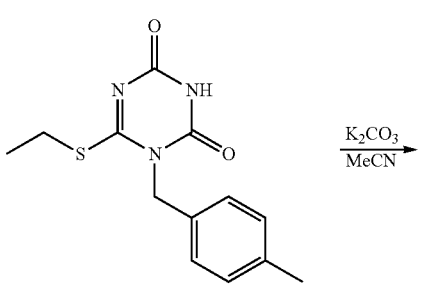
b3
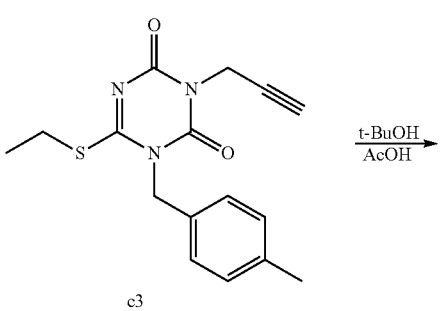
c3
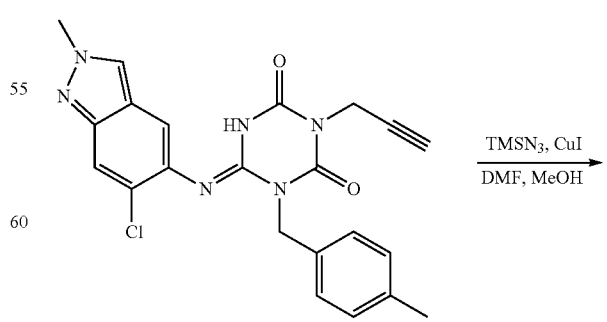
d3

-continued

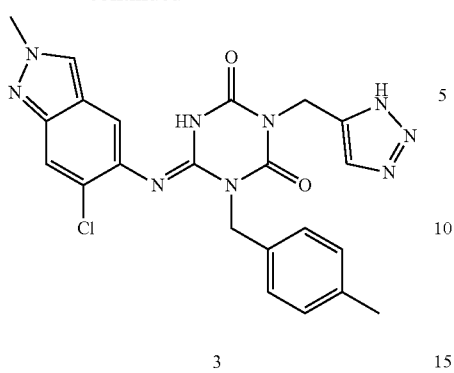

3

Compound 3 was prepared in the same way as Compound 1 (Example 1) with different starting materials, a yield of 42.75%.

$^1$H NMR (600 MHz, DMSO) δ 14.85-14.39 (m, 1H), 10.89 (s, 1H), 8.32 (s, 1H), 8.12-7.83 (m, 2H), 7.66-7.45 (m, 4H), 7.05 (s, 1H), 5.11 (d, J=53.9 Hz, 2H), 4.87 (s, 2H), 4.16 (d, J=31.2 Hz, 3H), 2.19 (s, 3H).

$^{13}$C NMR (151 MHz, DMSO) δ 153.97, 153.27, 149.29, 147.32, 146.62, 145.31, 144.72, 136.22, 133.57, 128.43, 125.67, 124.43, 123.76, 122.16, 115.42, 111.75, 107.45, 45.88, 41.11, 21.78.

Example 4

Compound 4: Preparation of (E)-3-(1H-1,2,3-triazol-5-yl)methyl)-1-(4-(tert-butyl)benzyl)-6-(6-chloro-2-methyl)-yl-2H-indazol-5-yl)imino)-1,3,5-triazine-2,4-dione

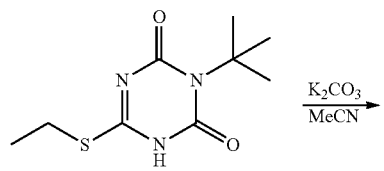

a4

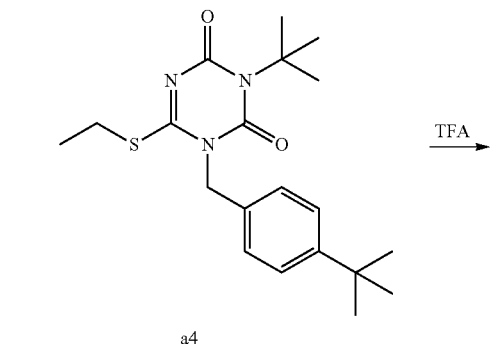

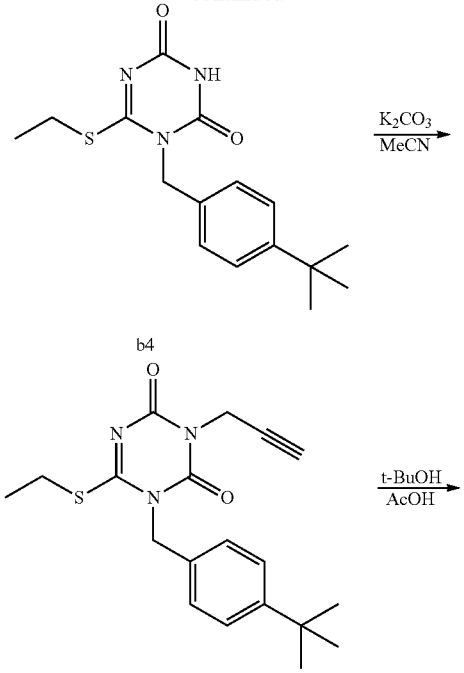

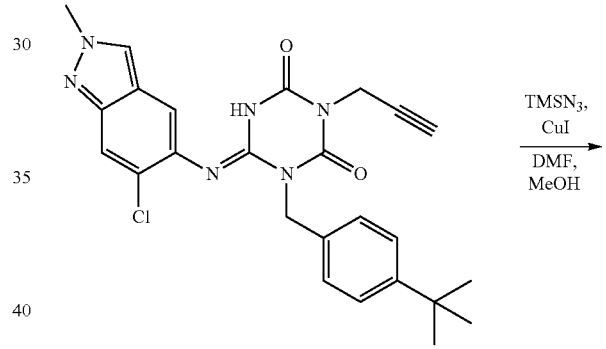

4

Compound 4 was prepared in the same way as Compound 1 (Example 1) with different starting materials, a yield of 35.46%.

$^1$H NMR (600 MHz, DMSO) δ 14.63-14.22 (m, 1H), 11.12 (s, 1H), 8.65 (s, 1H), 8.09-7.87 (m, 2H), 7.65-7.43 (m, 4H), 7.01 (s, 1H), 5.09 (d, J=53.8 Hz, 2H), 4.86 (s, 2H), 4.06 (d, J=31.6 Hz, 3H), 1.33 (s, 9H).

<sup>13</sup>C NMR (151 MHz, DMSO) δ 152.56, 147.23, 146.92, 142.45, 139.85, 135.41, 134.02, 133.58, 130.56, 127.45, 126.46, 124.25, 122.26, 119.47, 117.74, 116.85, 116.36, 116.01, 111.72, 40.22, 35.47, 31.32.

Example 5

Compound 5: Preparation of (E)-3-(1H-1,2,3-triazol-5-yl)methyl)-6-(6-chloro-2-methyl-2H-indazol-5-yl)imino)-1-(4-nitrobenzyl)-1,3,5-triazine-2,4-dione

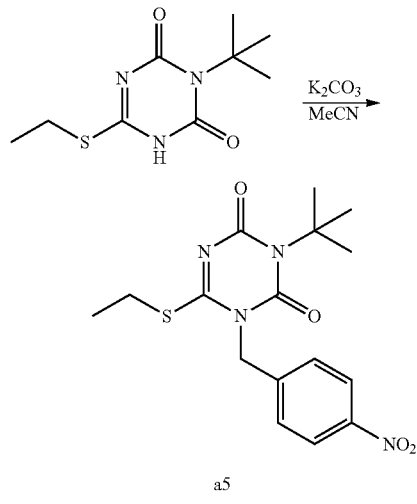

a5

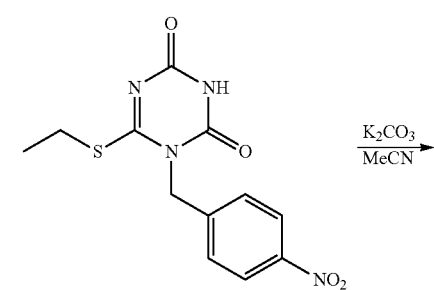

b5

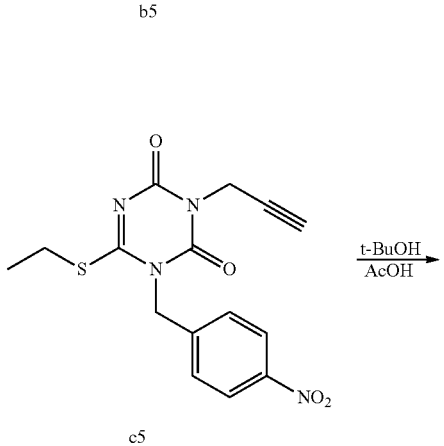

c5

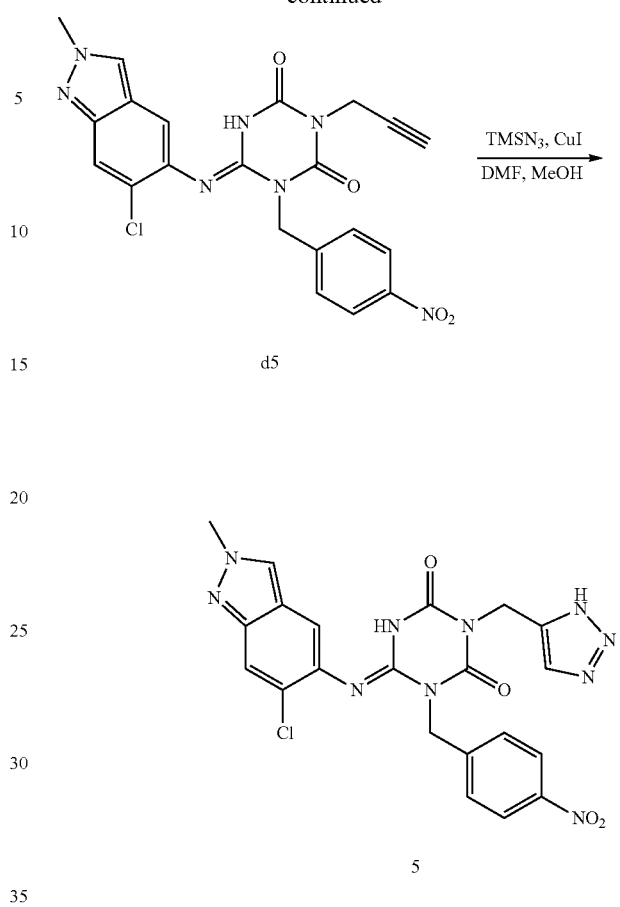

d5

Compound 5 was prepared in the same way as Compound 1 (Example 1) with different starting materials, a yield of 32.10%.

<sup>1</sup>H NMR (600 MHz, DMSO) δ 14.94-14.53 (m, 1H), 11.06 (s, 1H), 8.78 (s, 1H), 7.95-7.83 (m, 2H), 7.53-7.21 (m, 4H), 7.07 (s, 1H), 5.12 (d, J=53.2 Hz, 2H), 4.92 (s, 2H), 4.21 (d, J=31.1 Hz, 3H).

<sup>13</sup>C NMR (151 MHz, DMSO) δ 153.97, 152.85, 151.51, 150.88, 148.78, 147.11, 145.49, 140.41, 138.32, 133.57, 128.17, 125.56, 122.16, 118.52, 114.72, 109.79, 50.18, 39.91, 36.25.

Example 6

Compound 6: Preparation of (E)-3-(1H-1,2,3-triazol-5-yl)methyl)-6-(6-chloro-2-methyl-2H-indazol-5-yl)imino)-1-(4-methoxybenzyl)-1,3,5-triazine-2,4-dione

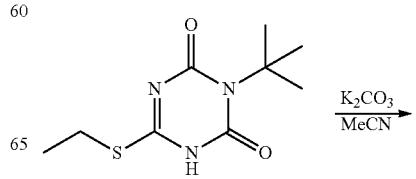

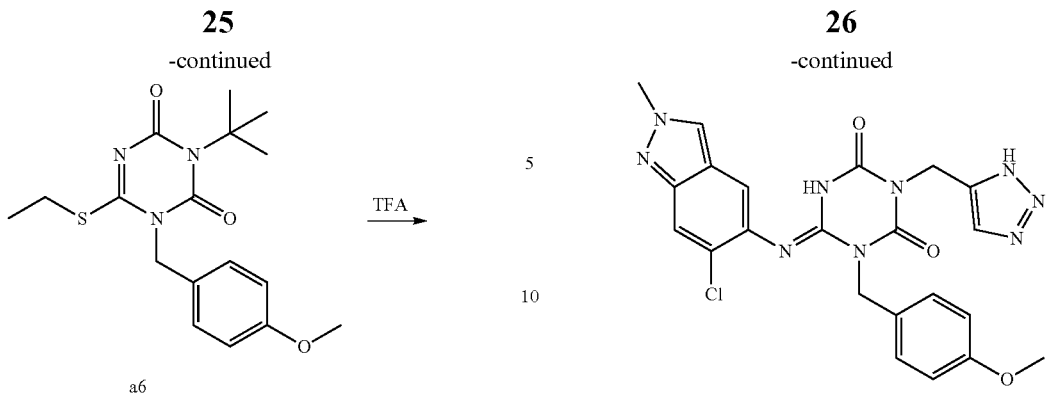
Compound 6 was prepared in the same way as Compound 1 (Example 1) with different starting materials, a yield of 32.05%.
$^1$H NMR (600 MHz, DMSO) δ 14.74-14.32 (m, 1H), 10.89 (s, 1H), 8.44 (s, 1H), 8.03-7.62 (m, 2H), 7.32-7.13 (m, 4H), 6.98 (s, 1H), 5.11 (d, J=54.3 Hz, 2H), 4.76 (s, 2H), 4.23 (d, J=31.8 Hz, 3H), 3.81 (s, 3H)
$^{13}$C NMR (151 MHz, DMSO) δ 155.47, 154.55, 153.71, 152.48, 149.58, 148.61, 146.12, 142.56, 139.98, 135.65, 129.23, 126.37, 123.73, 119.63, 116.85, 111.56, 54.23, 49.52, 41.02, 39.85.
Example 7
Compound 7: Preparation of (E)-3-(1H-1,2,3-triazol-5-yl)methyl)-6-(6-chloro-2-methyl-2H-indazol-5-yl)imino)-1-(4-(trifluoromethoxy)benzyl)-1,3,5-triazine-2,4-dione
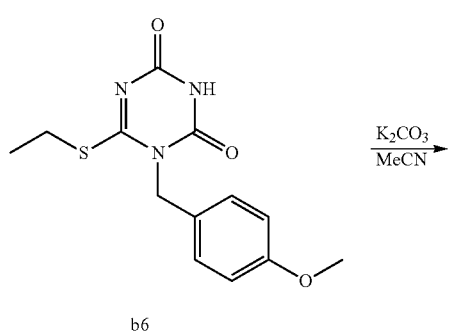
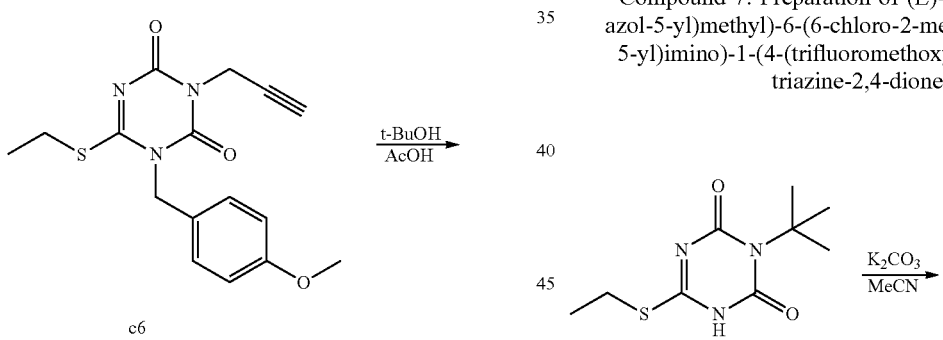
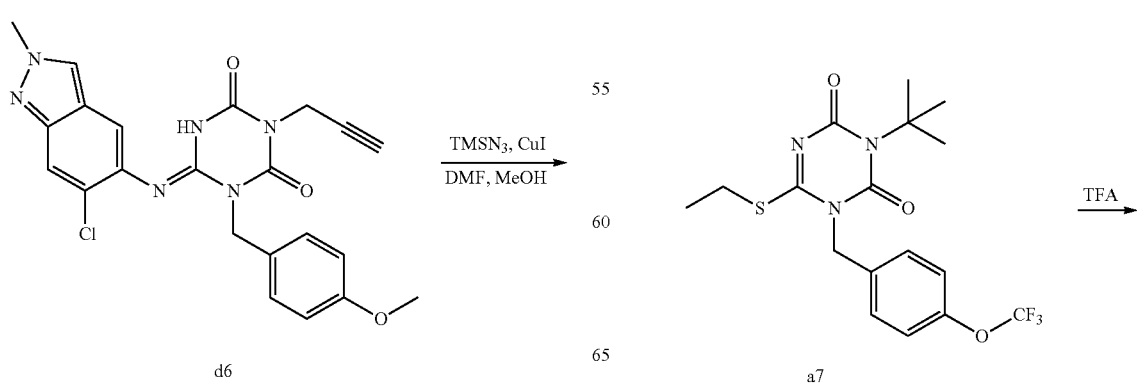

27
-continued
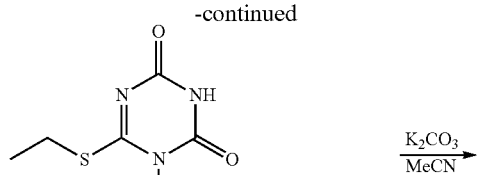
b7
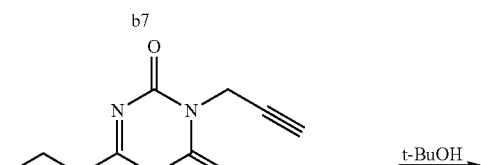
c7
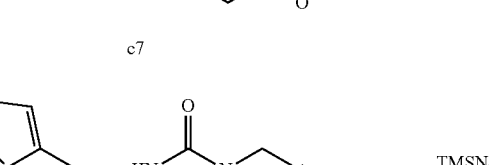
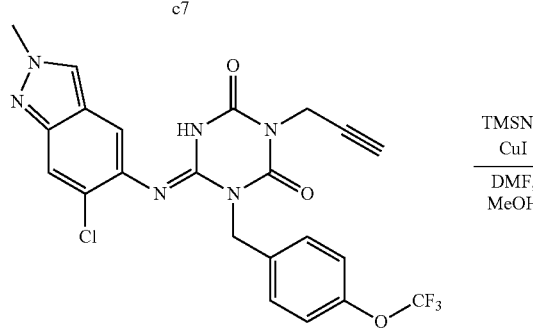
7
Compound 7 was prepared in the same way as Compound 1 (Example 1) with different starting materials, a yield of 26.36%.
$^1$H NMR (600 MHz, DMSO) δ 14.35-14.12 (m, 1H), 10.65 (s, 1H), 8.23 (s, 1H), 7.92-7.61 (m, 2H), 7.12-6.89 (m, 4H), 6.73 (s, 1H), 4.96 (d, J=53.9 Hz, 2H), 4.61 (s, 2H), 4.02 (d, J=31.2 Hz, 3H).
$^{13}$C NMR (151 MHz, DMSO) δ 156.01, 154.12, 152.45, 151.63, 149.46, 147.95, 145.48, 141.77, 138.45, 132.19, 129.45, 128.61, 125.63, 124.18, 118.17, 112.69, 111.93, 48.63, 40.14, 38.63.
28
Example 8
Compound 8: Preparation of (E)-3-(1H-1,2,3-triazol-5-yl)methyl)-6-(6-chloro-2-methyl-2H-indazol-5-yl)imino)-1-(4-fluorobenzyl)-1,3,5-triazine-2,4-dione
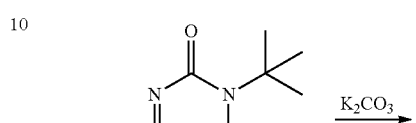
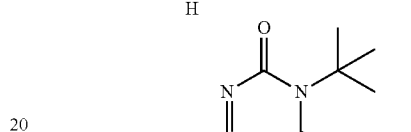
a8
b8
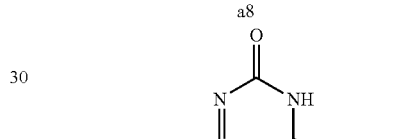
c8
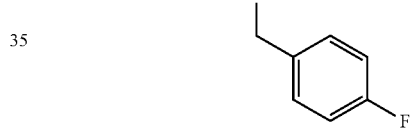
d8

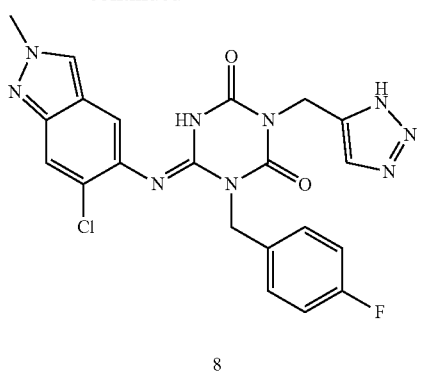 [SMILES: Cn1cc2cc(/N=c3\[nH]c(=O)n(Cc4cnn[nH]4)c(=O)n3Cc3ccc(F)cc3)c(Cl)cc2n1]

8

Compound 8 was prepared in the same way as Compound 1 (Example 1) with different starting materials, a yield of 40.42%.

¹H NMR (600 MHz, DMSO) δ 14.93-14.52 (m, 1H), 10.94 (s, 1H), 8.56 (s, 1H), 8.12-7.88 (m, 2H), 7.43-7.25 (m, 4H), 7.02 (s, 1H), 5.34 (d, J=53.9 Hz, 2H), 4.85 (s, 2H), 4.09 (d, J=31.8 Hz, 3H).

¹³C NMR (151 MHz, DMSO) δ 159.57, 153.75, 152.67, 151.54, 147.69, 144.86, 142.45, 139.73, 136.83, 134.58, 127.32, 125.72, 122.85, 118.93, 115.15, 111.12, 47.38, 40.58, 38.92.

Example 9

Compound 9: Preparation of (E)-3-(1H-1,2,3-triazol-5-yl)methyl)-6-(6-chloro-2-methyl-2H-indazol-5-yl)imino)-1-(4-chlorobenzyl)-1,3,5-triazine-2,4-dione

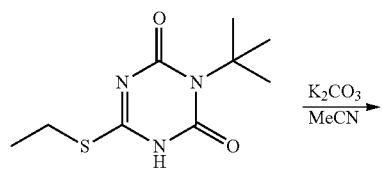

a9

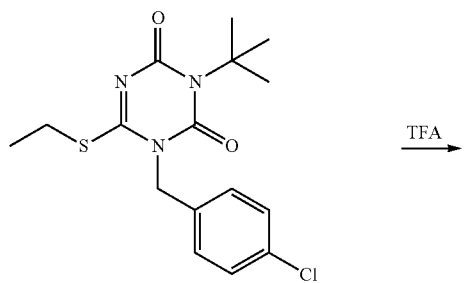

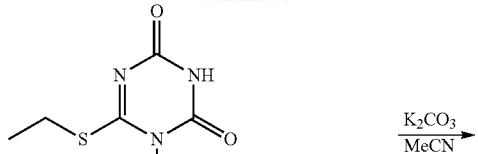

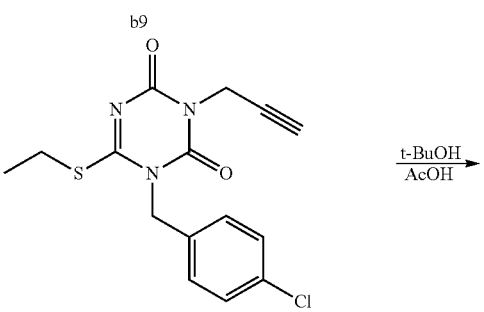

b9

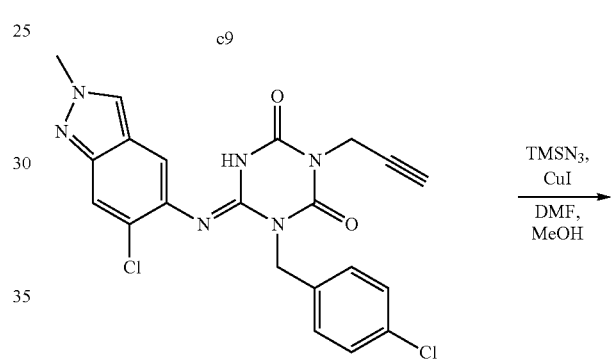

c9 d9

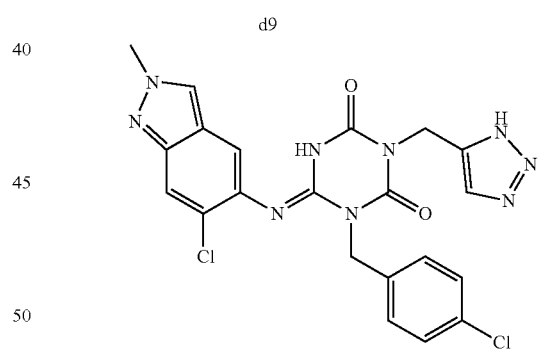

9

Compound 9 was prepared in the same way as Compound 1 (Example 1) with different starting materials, a yield of 38.42%.

¹H NMR (600 MHz, DMSO) δ 14.65-14.30 (m, 1H), 10.81 (s, 1H), 8.86 (s, 1H), 8.09-7.56 (m, 2H), 7.23-7.09 (m, 4H), 6.96 (s, 1H), 5.21 (d, J=53.5 Hz, 2H), 4.77 (s, 2H), 3.92 (d, J=31.5 Hz, 3H).

¹³C NMR (151 MHz, DMSO) δ 153.68, 151.12, 150.45, 149.32, 147.45, 144.75, 142.18, 139.14, 136.25, 134.24, 127.47, 125.85, 122.36, 118.47, 115.41, 111.49, 47.78, 40.49, 38.14.

Example 10

Compound 10: Preparation of (E)-3-((1H-1,2,3-triazol-5-yl)methyl)-1-(4-bromophenyl)-6-((6-chloro-2-methyl-2H-indazol-5-yl)imino)-1,3,5-triazine-2,4-dione

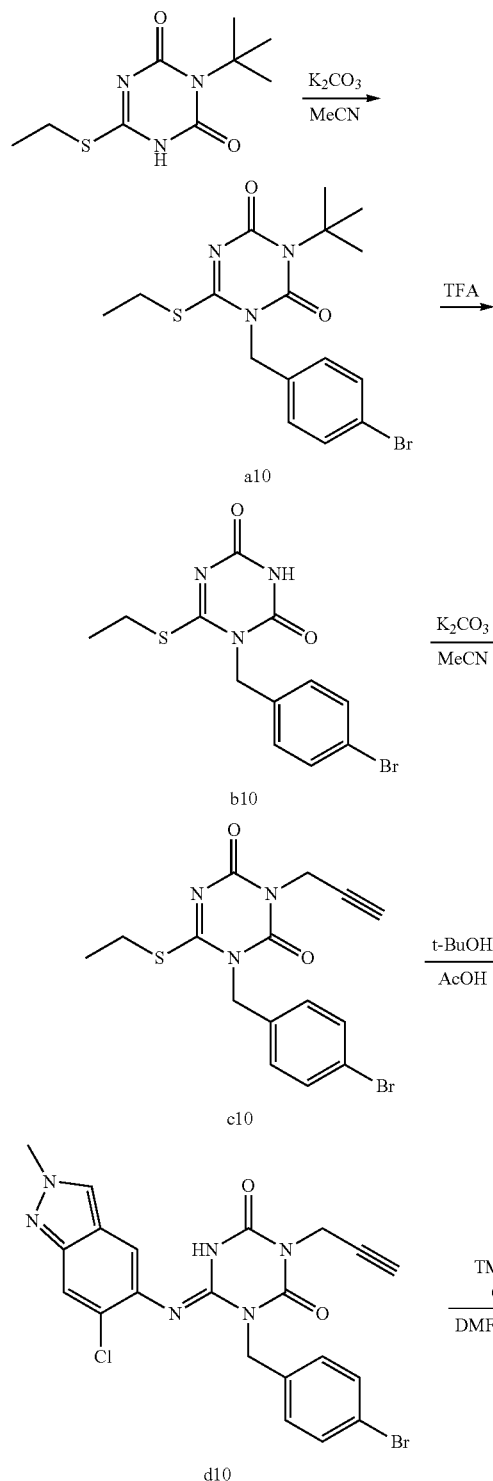

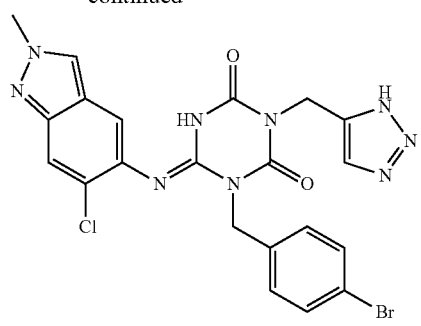

Compound 10 was prepared in the same way as Compound 1 (Example 1) with different starting materials, a yield of 39.77%.

$^1$H NMR (600 MHz, DMSO) δ 14.77-14.42 (m, 1H), 11.01 (s, 1H), 8.93 (s, 1H), 8.17-7.68 (m, 2H), 7.32-7.12 (m, 4H), 7.01 (s, 1H), 5.44 (d, J=53.6 Hz, 2H), 4.86 (s, 2H), 4.01 (d, J=31.8 Hz, 3H).

$^{13}$C NMR (151 MHz, DMSO) δ 154.12, 153.98, 148.53, 142.23, 141.56, 139.42, 138.17, 137.45, 136.46, 130.58, 129.37, 127.41, 125.86, 122.16, 119.45, 113.98, 45.19, 40.86, 38.63.

Example 11

Compound 11: Preparation of (E)-3-((1H-1,2,3-triazol-5-yl)methyl)-1-([1,1-biphenyl]-4-ylmethyl)-6-(((6-chloro-2-methyl-2H-indazol-5-yl)imino)-1,3,5-triazine-2,4-dione

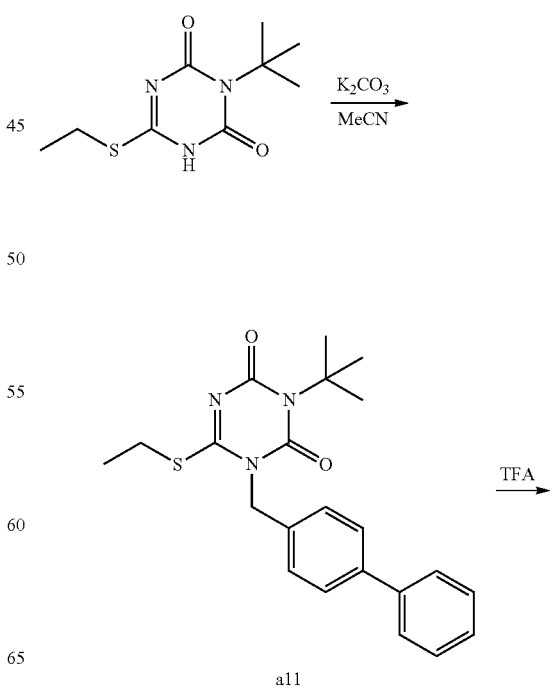

-continued
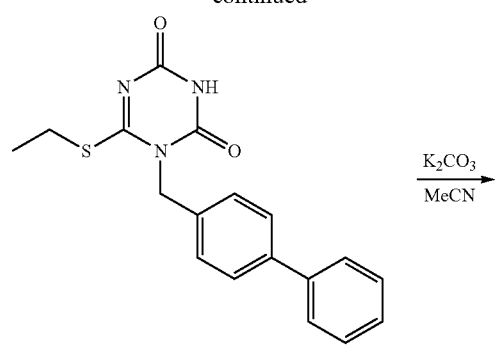
b11
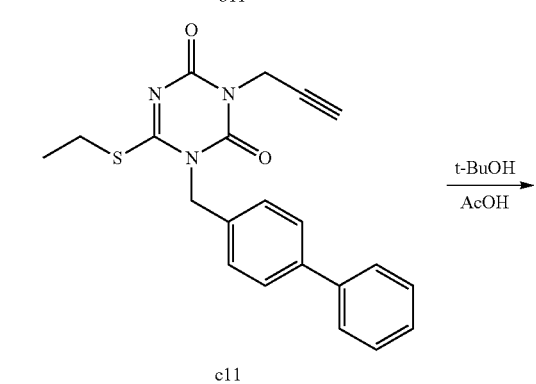
c11
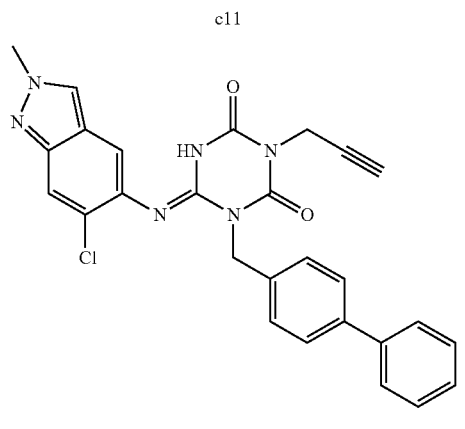
d11
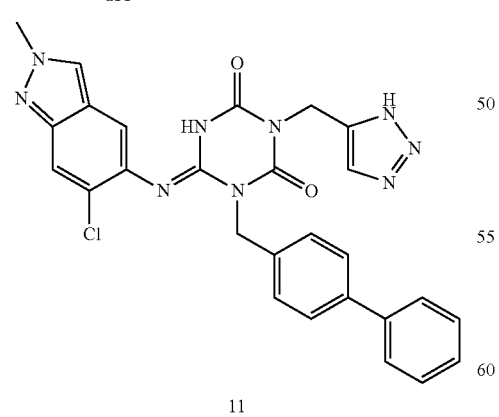
11
Compound 11 was prepared in the same way as Compound 1 (Example 1) with different starting materials, a yield of 25.01%.
$^1$H NMR (600 MHz, DMSO) δ 14.75-14.32 (m, 1H), 11.23 (s, 1H), 8.71 (s, 1H), 7.99-7.82 (m, 2H), 7.65-7.43 (m, 6H), 7.40-7.31 (s, 4H), 5.13 (d, J=53.9 Hz, 2H), 4.79 (s, 2H), 4.13 (d, J=31.9 Hz, 3H).
$^{13}$C NMR (151 MHz, DMSO) δ 153.74, 152.02, 148.43, 145.45, 143.89, 141.43, 138.51, 136.58, 132.68, 132.42, 131.71, 129.56, 128.26, 127.78, 126.72, 119.56, 115.85, 114.74, 112.85, 111.41, 48.36, 47.58, 41.68.
Example 12
Compound 12: Preparation of (E)-3-(1H-1,2,3-triazol-5-yl)methyl)-6-(6-chloro-2-methyl-2H-indazol-5-yl)imino)-1-(4-(trifluoromethyl)benzyl)-1,3,5-triazine-2,4-dione
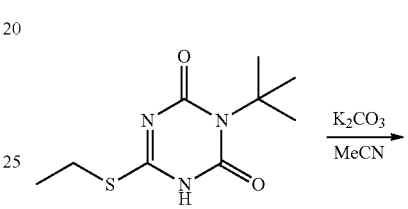
a12
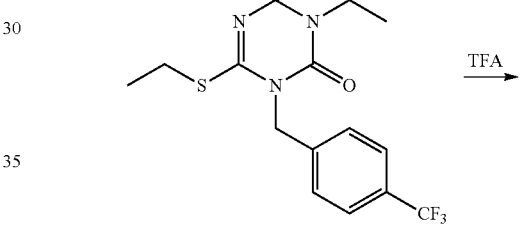
b12
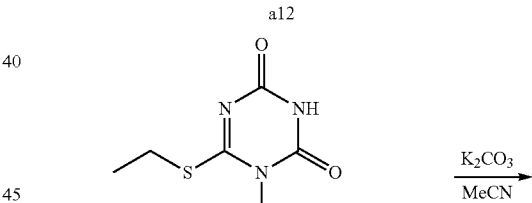
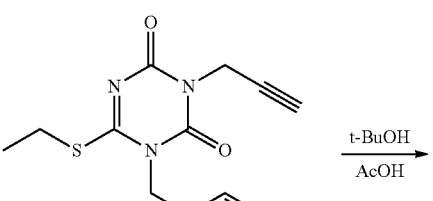
c12

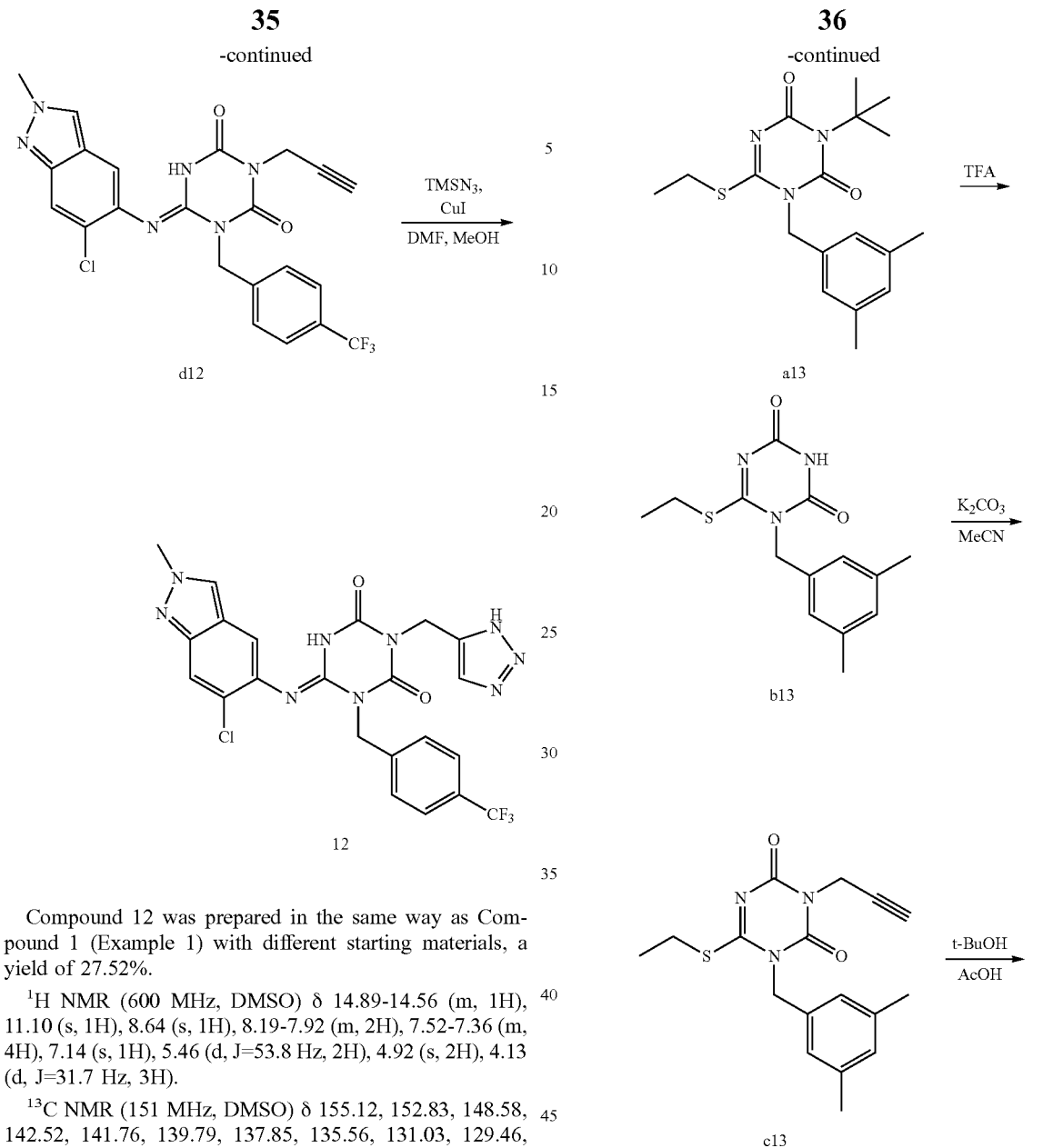
Compound 12 was prepared in the same way as Compound 1 (Example 1) with different starting materials, a yield of 27.52%.
$^1$H NMR (600 MHz, DMSO) δ 14.89-14.56 (m, 1H), 11.10 (s, 1H), 8.64 (s, 1H), 8.19-7.92 (m, 2H), 7.52-7.36 (m, 4H), 7.14 (s, 1H), 5.46 (d, J=53.8 Hz, 2H), 4.92 (s, 2H), 4.13 (d, J=31.7 Hz, 3H).
$^{13}$C NMR (151 MHz, DMSO) δ 155.12, 152.83, 148.58, 142.52, 141.76, 139.79, 137.85, 135.56, 131.03, 129.46, 128.73, 126.86, 125.87, 124.41, 123.38, 119.24, 113.16, 46.10, 41.78, 40.23.
Example 13
Compound 13: Preparation of (E)-3-(1H-1,2,3-triazol-5-yl)methyl)-6-(6-chloro-2-methyl-2H-indazol-5-yl)imino)-1-(3,5-dimethylbenzyl)-1,3,5-triazine-2,4-dione
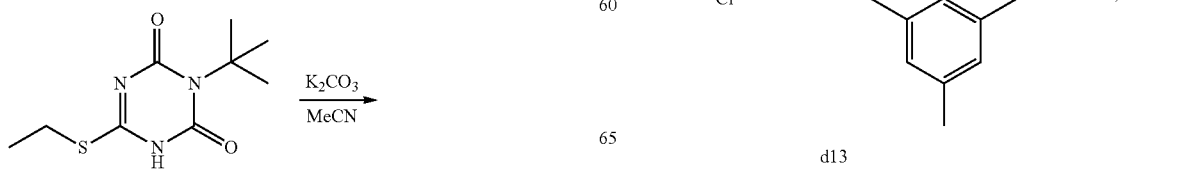

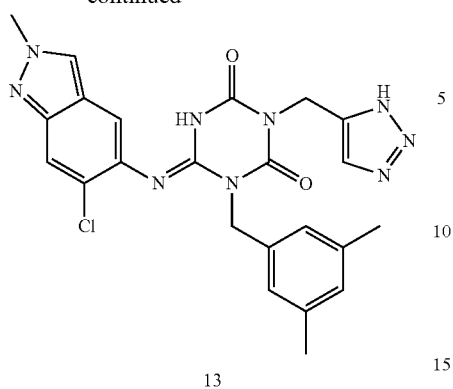

13

Compound 13 was prepared in the same way as Compound 1 (Example 1) with different starting materials, a yield of 26.44%.

$^1$H NMR (600 MHz, DMSO) δ 14.91-14.45 (m, 1H), 11.05 (s, 1H), 8.45 (s, 1H), 8.15-7.89 (m, 2H), 7.74-7.56 (m, 3H), 7.12 (s, 1H), 5.15 (d, J=54.1 Hz, 2H), 4.93 (s, 2H), 4.21 (d, J=31.5 Hz, 3H), 2.21-2.19 (s, 6H).

$^{13}$C NMR (151 MHz, DMSO) δ 153.76, 151.23, 149.58, 145.59, 143.53, 141.81, 139.52, 135.45, 133.76, 129.57, 128.53, 123.89, 121.43, 120.83, 117.36, 115.81, 47.25, 45.43, 43.57, 25.69.

Example 14

Compound 14: Preparation of (E)-3-(1H-1,2,3-triazol-5-yl)methyl)-6-(6-chloro-2-methyl-2H-indazol-5-yl)imino)-1-(3,5-dimethoxybenzyl)-1,3,5-triazine-2,4-dione

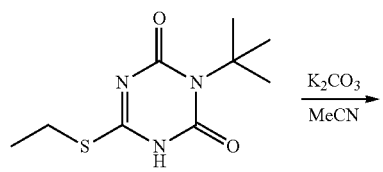

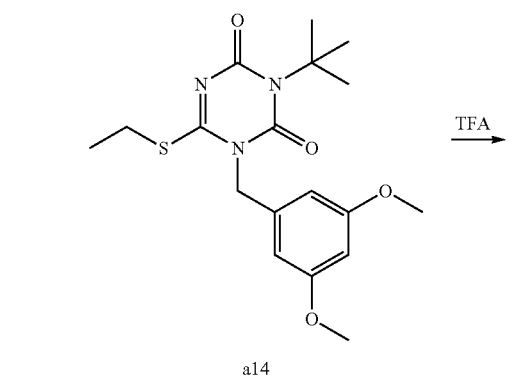

a14

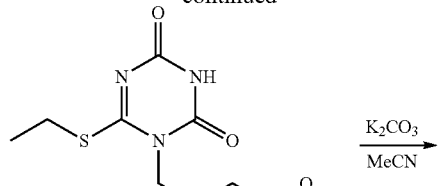

b14

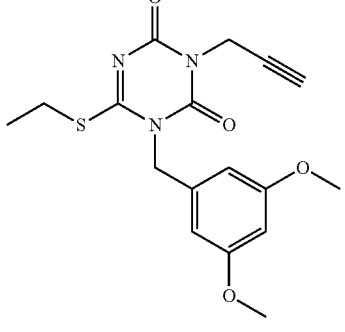

c14

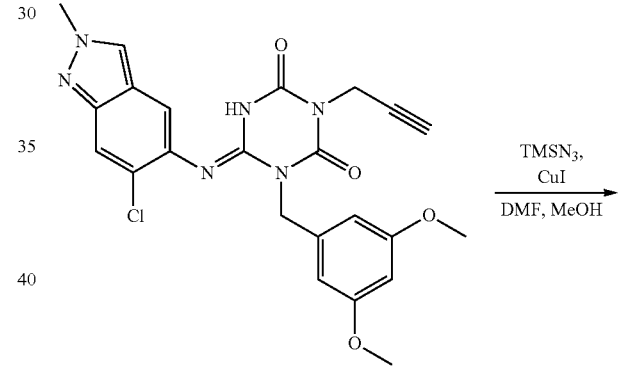

d14

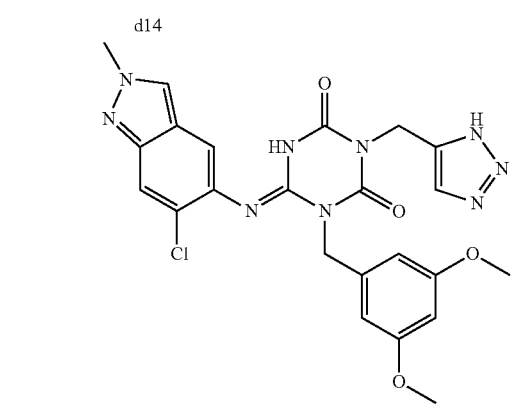

14

Compound 14 was prepared in the same way as Compound 1 (Example 1) with different starting materials, a yield of 24.93%.

$^1$H NMR (600 MHz, DMSO) δ 14.96-14.51 (m, 1H), 11.09 (s, 1H), 8.64 (s, 1H), 8.22-7.72 (m, 2H), 7.63-7.51 (m,

3H), 7.21 (s, 1H), 5.13 (d, J=54.2 Hz, 2H), 4.89 (s, 2H), 4.11 (d, J=31.4 Hz, 3H), 3.81 (s, 6H).

$^{13}$C NMR (151 MHz, DMSO) δ 161.45, 155.75, 152.41, 149.47, 145.15, 143.78, 141.47, 135.12, 132.49, 128.57, 126.47, 121.74, 119.38, 115.56, 109.53, 104.41, 54.13, 45.58, 43.76, 41.15.

Example 15

Compound 15: Preparation of (E)-3-(1H-1,2,3-triazol-5-yl)methyl)-6-(6-chloro-2-methyl-2H-indazol-5-yl)imino)-1-(3,5-difluorobenzyl)-1,3,5-triazine-2,4-dione

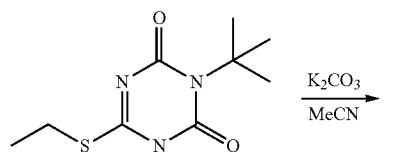
a15

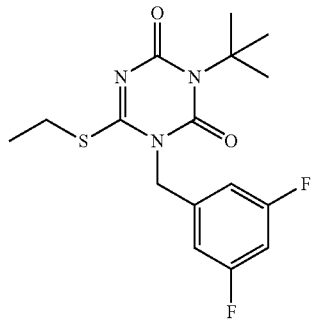
b15

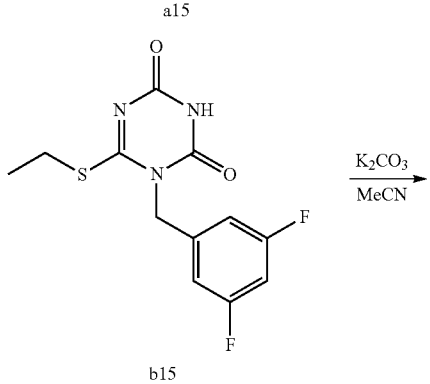
c15

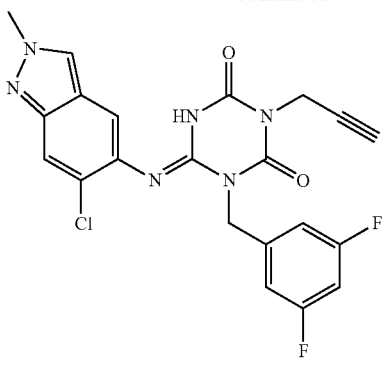
d15

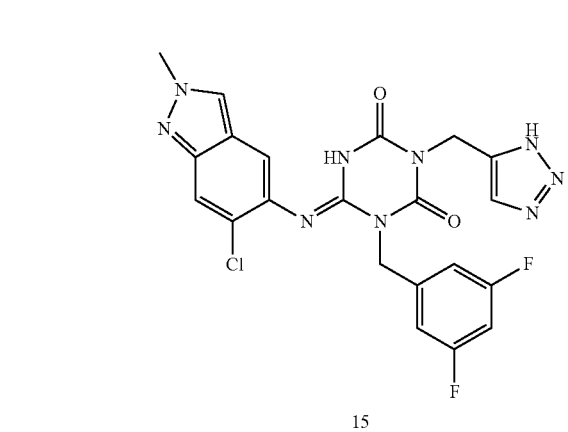
15

Compound 15 was prepared in the same way as Compound 1 (Example 1) with different starting materials, a yield of 26.78%.

$^1$H NMR (600 MHz, DMSO) δ 14.86-14.47 (m, 1H), 10.95 (s, 1H), 8.35 (s, 1H), 7.78-7.21 (m, 5H), 7.15 (s, 1H), 5.65 (d, J=54.2 Hz, 2H), 4.84 (s, 2H), 4.11 (d, J=31.7 Hz, 3H).

$^{13}$C NMR (151 MHz, DMSO) δ 159.47, 155.82, 154.73, 148.78, 146.45, 143.61, 141.83, 137.82, 132.41, 128.85, 126.49, 120.53, 118.88, 116.52, 109.62, 106.87, 52.98, 41.91, 39.15.

Example 16

Compound 16: Preparation of (E)-6-(6-chloro-2-methyl-2H-indazol-5-yl)imino)-3-(1-methyl-1H-1,2,3-triazole-5-yl)methyl)-1-(2,4,5-trifluorobenzyl)-1,3,5-triazine-2,4-dione (1) Preparation of Compound a16

The preparation method is the same as in Example 1.

(2) Preparation of Compound c16

The preparation method is the same as in Example 1.

(3) Preparation of Compound d16

The preparation method is the same as in Example 1.

(4) Preparation of Compound e16

The preparation method is the same as the preparation of compound 1 in Example 1.

(5) Preparation of Compound 16

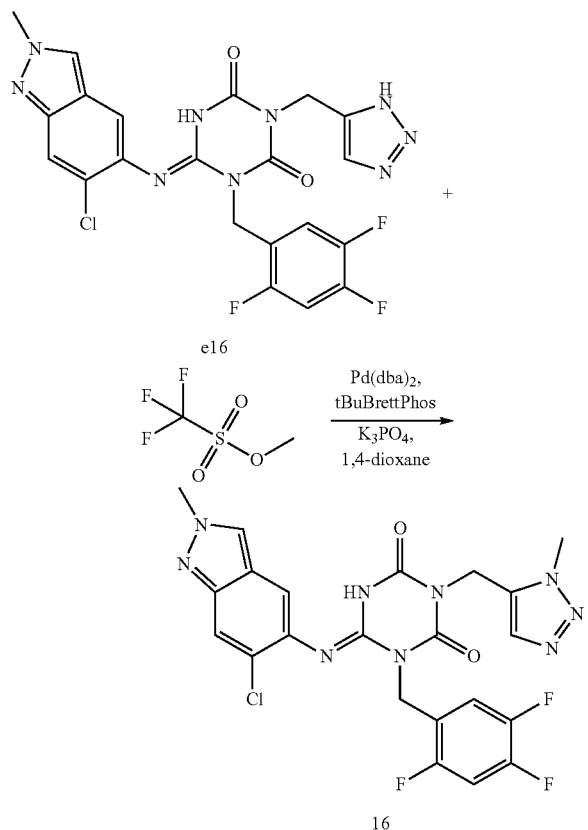

Bisdibenzylideneacetone palladium (6.9 mg, 0.012 mmol), 2-(di-tert-butylphosphine)-3,6-dimethoxy-2'-4'-6'tri-1-Propyl-1,1'-bisphenyl (8.7 mg, 0.018 mmol), and potassium phosphate (95.5 mg, 0.45 mmol) were placed in a reactor with 1.5 mL of 1,4-dioxane, stirred and heated at 120° C. for 5 min, then cooled to room temperature. Methyl trifluoromethanesulfonate (49.2 mg, 0.3 mmol) and compound e16 (186.4 mg, 0.36 mmol) prepared in step (4) were added, and the reaction mixture was then stirred at 70° C. for 24 h. After the reaction was complete, the reaction solution was diluted and extracted with dichloromethane solution, the organic phase was concentrated under reduced pressure, separated and purified by column chromatography (dichloromethane: methanol (V:V)=12:1 as mobile phase), and dried to obtain 33.6 mg of compound 16, a yield of 21.03%.

$^1$H NMR (600 MHz, DMSO) δ 11.95-10.12 (m, 1H), 8.10 (s, 1H), 7.74-7.41 (m, 4H), 7.01 (s, 1H), 5.45 (d, J=53.9 Hz, 2H), 4.85 (s, 2H), 4.22 (d, J=31.7 Hz, 6H).

$^{13}$C NMR (151 MHz, DMSO) δ 156.78, 154.72, 153.51, 149.43, 148.85, 146.45, 145.89, 143.82, 141.71, 137.82, 134.53, 131.74, 125.71, 122.86, 121.46, 116.78, 112.16, 107.82, 55.18, 37.51, 35.05, 31.76.

Example 17

Compound 17: Preparation of (E)-6-(6-chloro-2-methyl-2H-indazol-5-yl)imino)-3-(1-ethyl-1H-1,2,3-triazole-5-yl)methyl)-1-(2,4,5-trifluorobenzyl)-1,3,5-triazine-2,4-dione

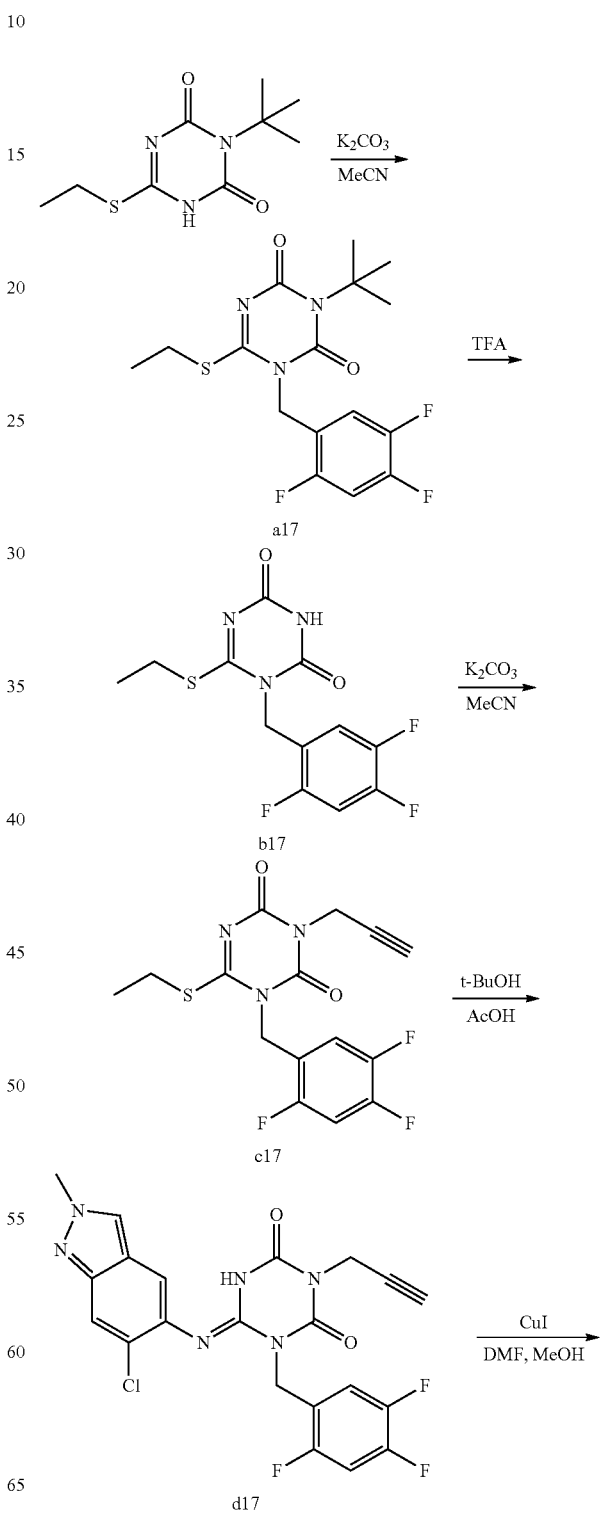

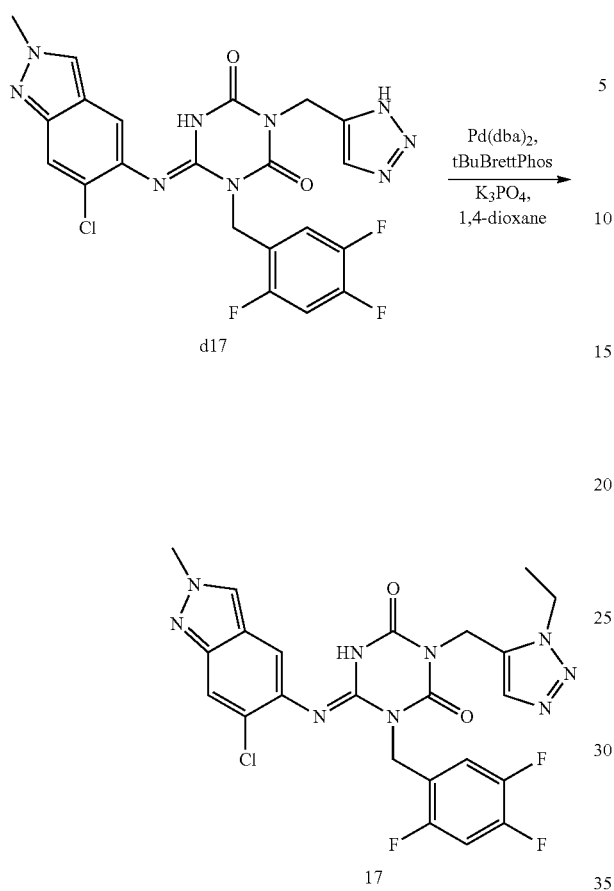
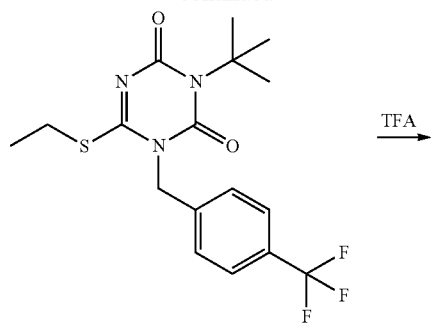
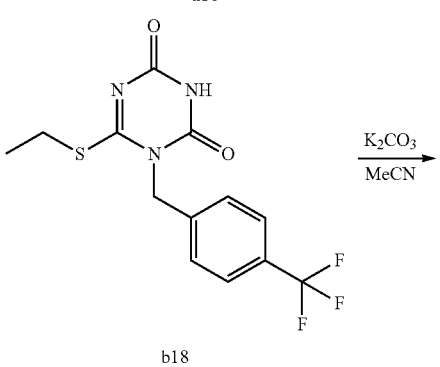
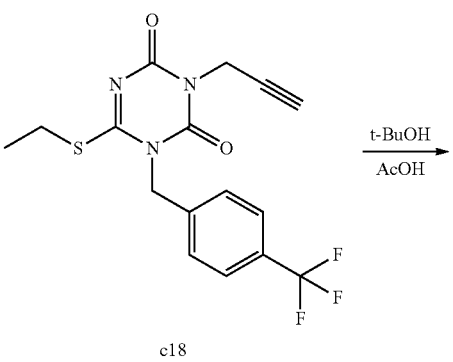
Compound 17 was prepared in the same way as Compound 16 (Example 16) with different starting materials, a yield of 23.52%.
$^1$HNMR (600 MHz, DMSO) δ 11.78-10.23 (m, 1H), 8.17 (s, 1H), 7.45-7.31 (m, 4H), 6.98 (s, 1H), 5.75 (d, J=53.8 Hz, 2H), 4.65 (s, 2H), 4.17 (d, J=31.7 Hz, 5H), 2.23 (s, 3H).
$^{13}$C NMR (151 MHz, DMSO) δ 157.47, 154.56, 153.63, 149.12, 148.78, 146.86, 145.75, 143.46, 142.25, 137.74, 135.76, 131.58, 125.43, 122.86, 121.74, 117.73, 114.63, 109.39, 54.52, 35.23, 34.47, 31.25, 15.36.
Example 18
Compound 18: Preparation of (E)-6-(6-chloro-2-methyl-2H-indazol-5-yl)imino)-3-(1-ethyl-1H-1,2,3-triazole-5-(yl)methyl)-1-(4-(trifluoromethyl)benzyl)-1,3,5-triazine-2,4-dione
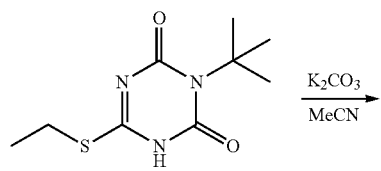
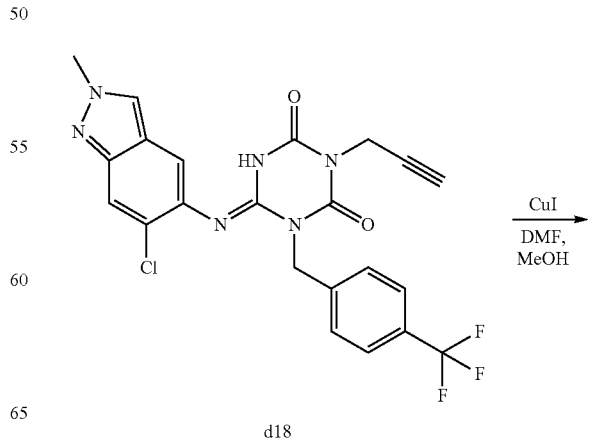

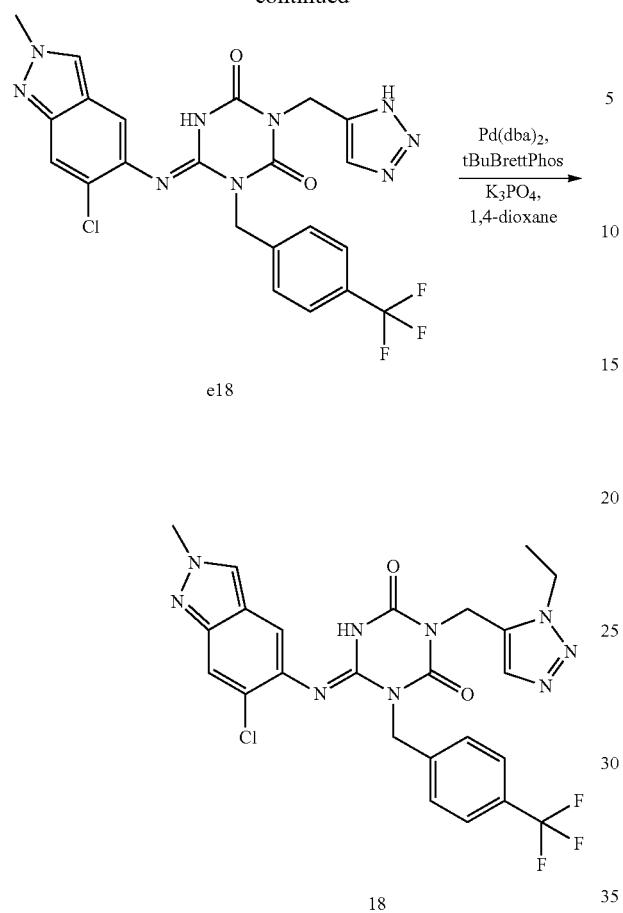
e18
18
Compound 18 was prepared in the same way as Compound 16 (Example 16) with different starting materials, a yield of 22.41%.
¹H NMR (600 MHz, DMSO) δ 11.07-10.96 (m, 1H), 7.56 (s, 1H), 7.49-7.14 (m, 4H), 6.67 (s, 1H), 5.48 (d, J=53.7 Hz, 2H), 4.27 (s, 2H), 4.11 (d, J=31.5 Hz, 3H), 2.24 (s, 1H), 1.61 (s, 3H), 1.04 (s, 3H).
¹³C NMR (151 MHz, DMSO) δ 159.13, 154.35, 153.25, 149.31, 148.35, 146.35, 145.64, 143.67, 142.15, 138.75, 136.58, 132.96, 127.24, 123.85, 121.46, 118.45, 114.42, 108.74, 54.96, 36.24, 33.57, 31.85, 28.75, 15.32.
Example 19
Compound 19: Preparation of (E)-6-(2-methyl-2H-indazol-5-yl)imino)-3-(1-ethyl-1H-1,2,3-triazol-5-yl)methyl)-1-(4-fluorobenzyl)-1,3,5-triazine-2,4-dione
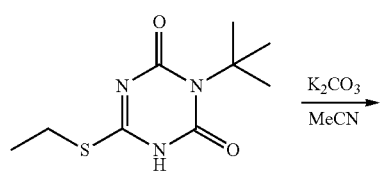
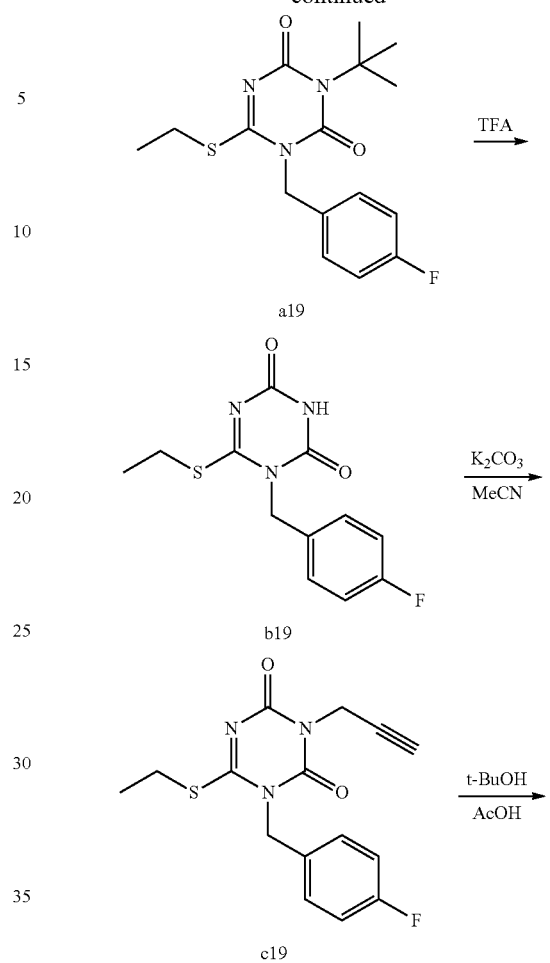
a19
b19
c19
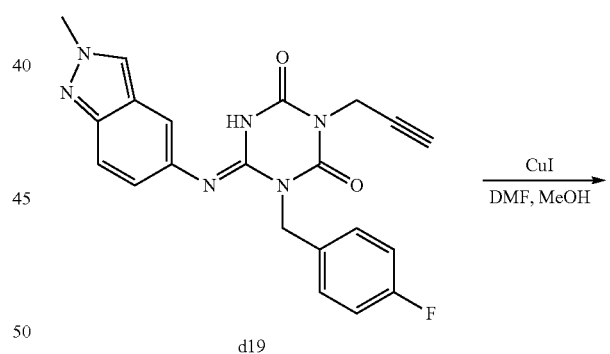
d19
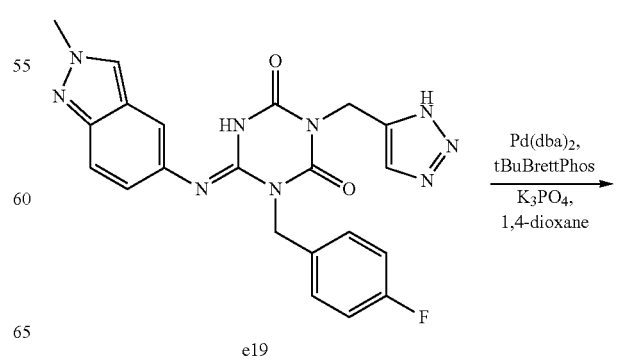
e19

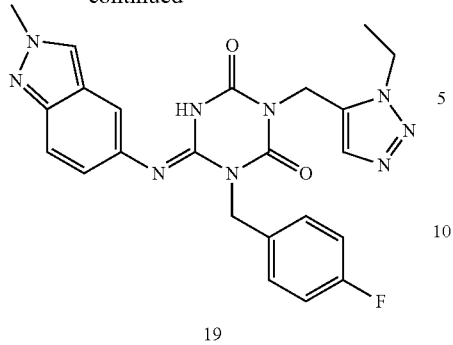

19

Compound 19 was prepared in the same way as Compound 16 (Example 16) with different starting materials, a yield of 24.70%.

$^1$H NMR (600 MHz, DMSO) δ 10.97-10.76 (m, 1H), 7.78 (s, 1H), 7.56-7.24 (m, 5H), 6.34 (s, 1H), 5.67 (d, J=53.6 Hz, 2H), 4.24 (s, 2H), 4.01 (d, J=31.7 Hz, 3H), 2.12 (s, 1H), 1.46 (s, 3H), 1.14 (s, 3H).

$^{13}$C NMR (151 MHz, DMSO) δ 159.32, 154.56, 153.76, 149.24, 148.75, 146.24, 145.42, 143.74, 142.57, 138.58, 136.97, 132.35, 127.24, 121.46, 118.75, 114.46, 108.35, 54.74, 36.35, 33.68, 31.46, 28.68, 15.57.

Example 20

Compound 20: Preparation of (E)-6-(6-chloro-2-methyl-2H-indazol-5-yl)imino)-3-(1-ethyl-1H-1,2,3-triazol-5-yl)methyl)-1-(4-fluorobenzyl)-1,3,5-triazine-2,4-dione

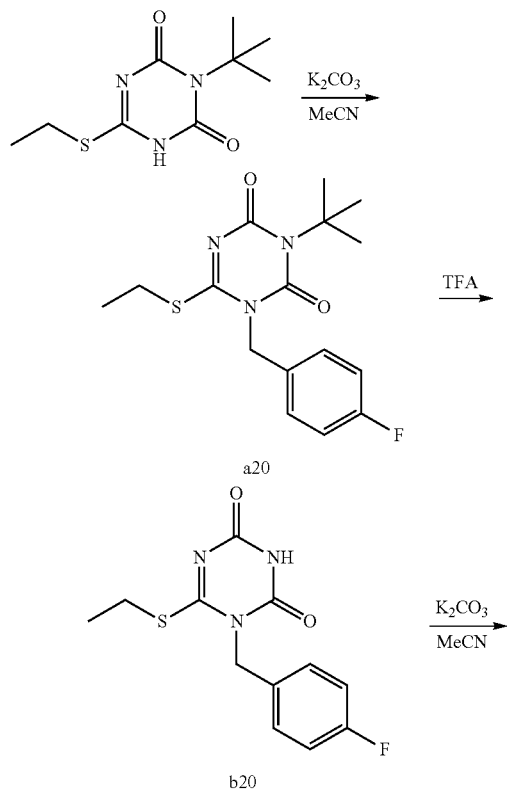

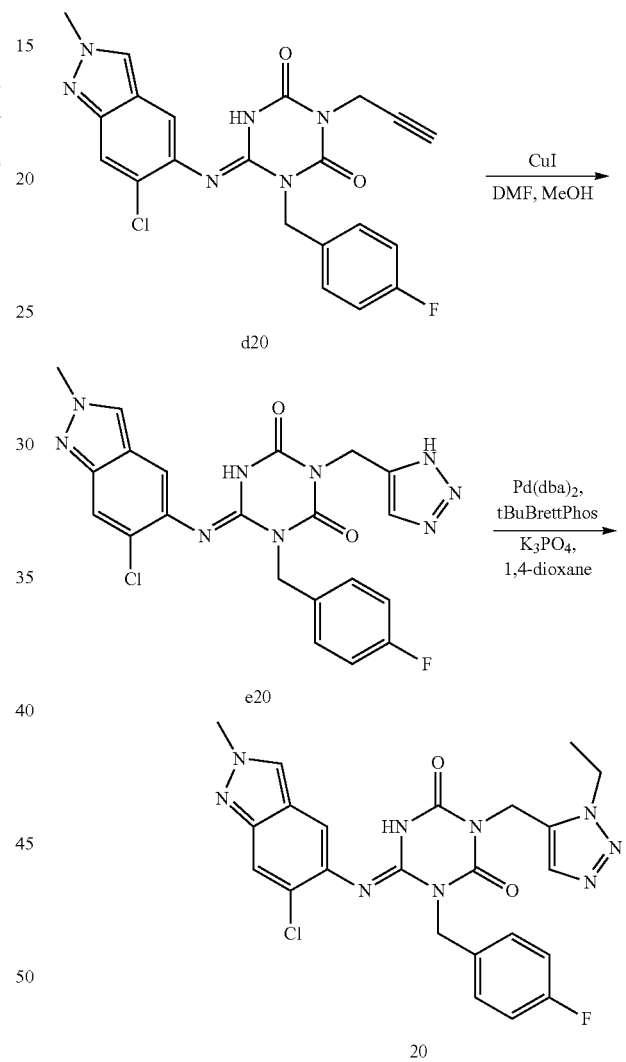

Compound 20 was prepared in the same way as Compound 16 (Example 16) with different starting materials, a yield of 23.76%.

$^1$H NMR (600 MHz, DMSO) δ 10.89-10.66 (m, 1H), 7.56 (s, 1H), 7.45-7.14 (m, 4H), 6.64 (s, 1H), 5.23 (d, J=53.7 Hz, 2H), 4.46 (s, 2H), 4.13 (d, J=31.5 Hz, 3H), 2.23 (s, 1H), 1.26 (s, 3H), 1.09 (s, 3H).

$^{13}$C NMR (151 MHz, DMSO) δ 159.46, 154.85, 153.35, 149.86, 148.46, 146.35, 145.46, 143.35, 142.25, 138.47, 136.63, 132.85, 127.58, 121.85, 118.25, 114.86, 108.35, 54.85, 36.46, 33.75, 31.68, 28.86, 15.24.

Example 21

Compound 21: Preparation of (E)-6-(6-chloro-2-methyl-2H-indazol-5-yl)imino)-3-(1-cyclopropyl-1H-1,2,3-triazole-5-yl)methyl)-1-(2,4,5-trifluorobenzyl)-1,3,5-triazine-2,4-dione (1) Preparation of Compound a21

The preparation method is the same as in Example 1.

(2) Preparation of Compound c21

The preparation method is the same as in Example 1.

(3) Preparation of Compound d21

The preparation method is the same as in Example 1.

(4) Preparation of Compound 21

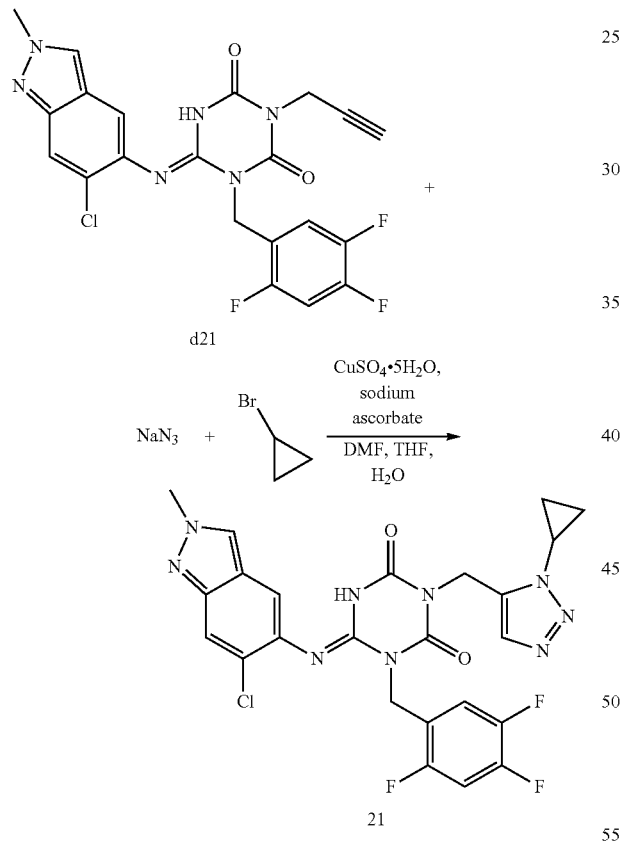

Sodium azide (598.1 mg, 9.2 mmol) and bromocyclopropane (240 μL, 3 mmol) were placed in a reactor, dissolved in 5 mL of dry DMF, and the reaction mixture was stirred at 60° C. overnight with TLC monitoring. After the reaction was complete, the reaction mixture was cooled to room temperature and extracted with brine and tetrahydrofuran, the tetrahydrofuran layer was collected, washed with 5% lithium chloride solution and dried with MgSO$_4$ to obtain azidocyclopropane.

Compound d21 (142.4 mg, 0.3 mmol), azidocyclopropane (29.9 mg, 0.36 mmol) and copper sulfate pentahydrate (30.0 mg, 0.12 mmol), and sodium ascorbate (23.8 mg, 0.12 mmol) were placed in the reactor and dissolved in a mixed solution of 10 mL of tetrahydrofuran and 1 mL of water under argon protection, heated and stirred at 45° C. overnight, and monitored by TLC. After the reaction was complete, the obtained reaction solution was concentrated under reduced pressure to remove the solvent, separated and purified by column chromatography (dichloromethane:methanol (V:V)=12:1 as mobile phase), and dried to obtain 35.2 mg of compound 21, a yield of 21.03%.

$^1$H NMR (600 MHz, DMSO) δ 11.01-10.36 (m, 1H), 7.98 (s, 1H), 7.56-7.25 (m, 4H), 7.12 (s, 1H), 5.38 (d, J=53.7 Hz, 2H), 4.76 (s, 2H), 4.52 (d, J=31.5 Hz, 3H), 2.56 (s, 1H), 1.21 (s, 2H), 0.86 (s, 2H).

$^{13}$C NMR (151 MHz, DMSO) δ 158.45, 155.86, 154.56, 149.86, 148.43, 146.76, 145.41, 143.78, 142.52, 138.47, 136.71, 132.78, 127.78, 123.52, 121.02, 118.57, 114.18, 108.75, 54.13, 36.85, 33.54, 31.17, 2.15.

Example 22

Compound 22: Preparation of (E)-6-(6-chloro-2-methyl-2H-indazol-5-yl)imino)-3-(1-isopropyl-1H-1,2,3-triazole-5-yl)methyl)-1-(2,4,5-trifluorobenzyl)-1,3,5-triazine-2,4-dione

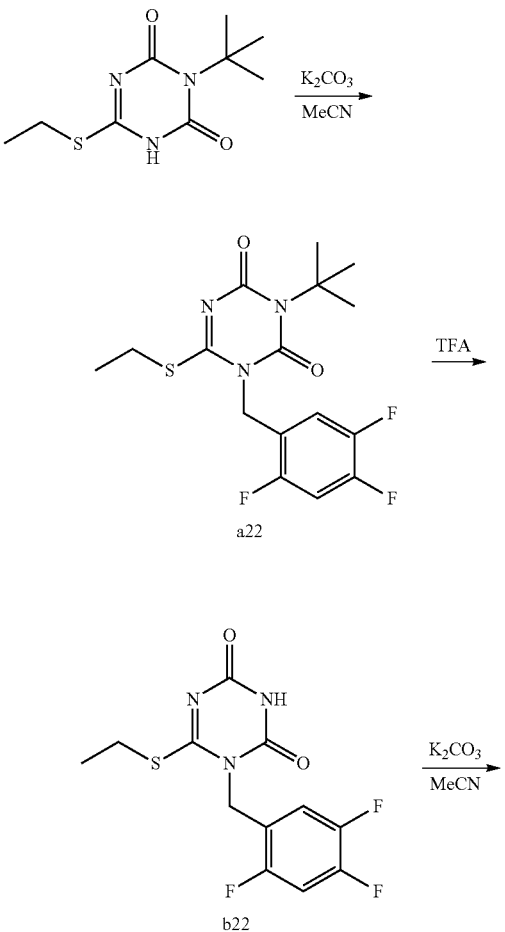

-continued
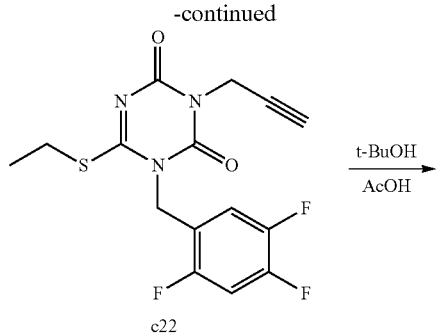
c22
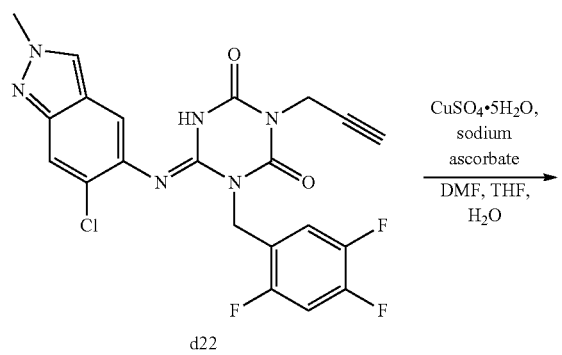
d22
22
Compound 22 was prepared in the same way as Compound 21 (Example 21) with different starting materials, a yield of 21.30%.
¹H NMR (600 MHz, DMSO) δ 11.21-10.76 (m, 1H), 7.68 (s, 1H), 7.36-7.15 (m, 4H), 6.88 (s, 1H), 5.18 (d, J=53.6 Hz, 2H), 4.36 (s, 2H), 4.01 (d, J=31.7 Hz, 3H), 2.16 (s, 1H), 1.71 (s, 3H), 1.06 (s, 3H).
¹³C NMR (151 MHz, DMSO) δ 158.32, 154.86, 153.78, 149.12, 148.03, 146.54, 145.15, 143.36, 142.22, 138.67, 136.63, 132.53, 127.85, 123.32, 121.45, 118.80, 114.53, 108.67, 54.14, 36.56, 33.24, 31.09, 28.14.
Example 23
Compound 23: Preparation of (E)-6-(6-chloro-2-methyl-2H-indazol-5-yl)imino)-3-(1-isobutyl-1H-1,2,3-triazole-5-yl)methyl)-1-(2,4,5-trifluorobenzyl)-1,3,5-triazine-2,4-dione
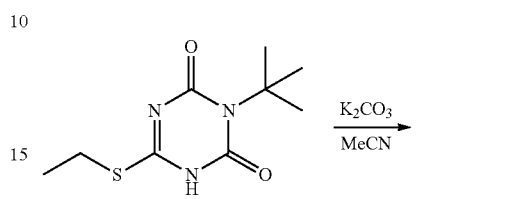
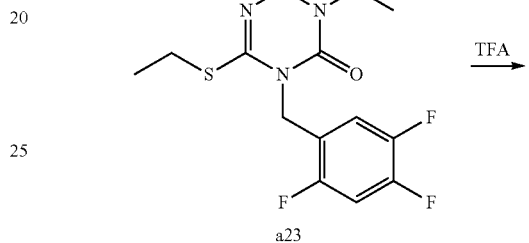
a23
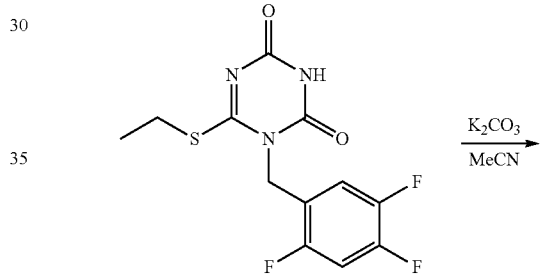
b23
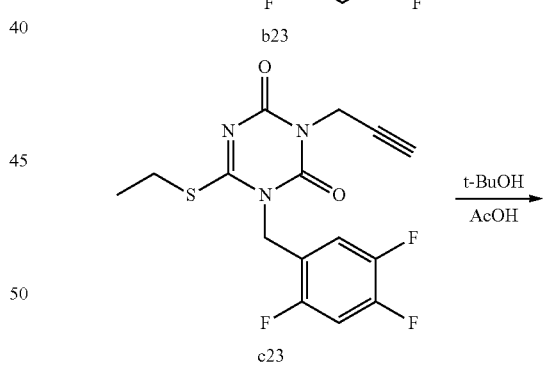
c23
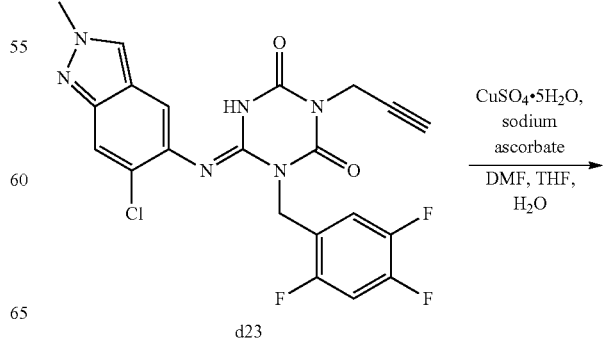
d23

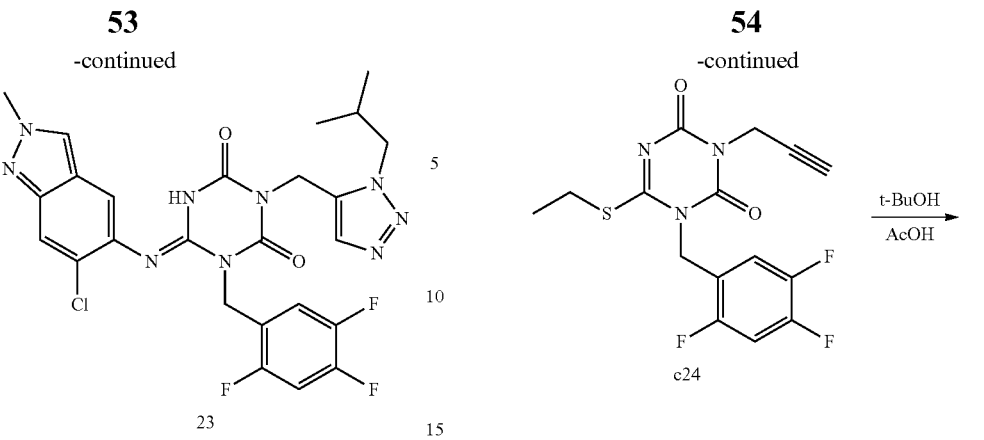

Compound 23 was prepared in the same way as Compound 21 (Example 21) with different starting materials, a yield of 19.22%.

¹H NMR (600 MHz, DMSO) δ 10.34-10.32 (m, 1H), 7.63 (s, 1H), 7.25-7.11 (m, 4H), 6.56 (s, 1H), 5.27 (d, J=53.7 Hz, 2H), 4.25 (s, 2H), 4.04 (d, J=31.2 Hz, 3H), 2.16 (s, 1H), 1.16 (s, 3H), 1.24 (s, 3H), 0.81 (s, 2H)

¹³C NMR (151 MHz, DMSO) δ 159.26, 154.67, 153.36, 149.17, 148.58, 146.37, 145.57, 143.36, 142.36, 138.58, 136.25, 132.48, 127.24, 123.69, 121.36, 118.58, 114.68, 108.35, 54.66, 36.96, 33.24, 31.68, 28.46, 19.78.

Example 24

Compound 24: Preparation of (E)-6-(6-chloro-2-methyl-2H-indazol-5-yl)imino)-3-(1-cyclobutyl-1H-1,2,3-triazole-5-yl)methyl)-1-(2,4,5-trifluorobenzyl)-1,3,5-triazine-2,4-dione

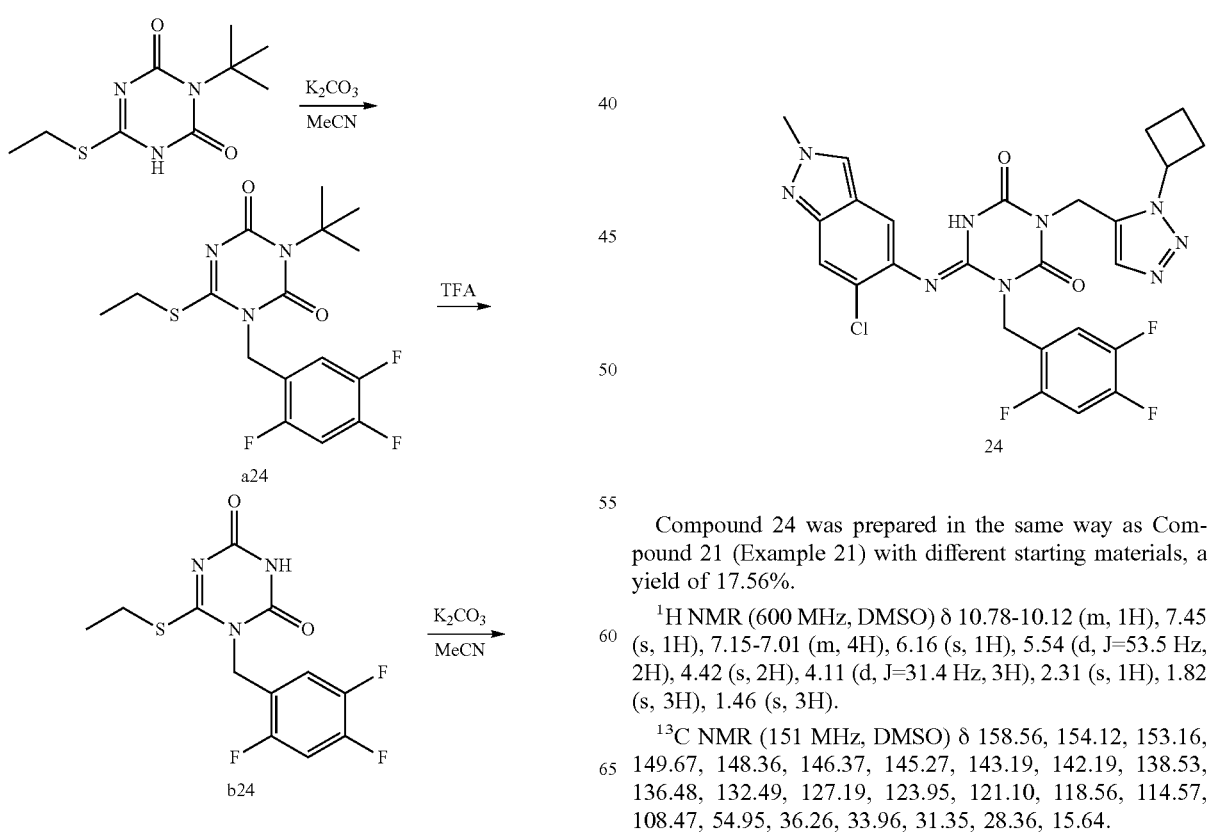

Compound 24 was prepared in the same way as Compound 21 (Example 21) with different starting materials, a yield of 17.56%.

¹H NMR (600 MHz, DMSO) δ 10.78-10.12 (m, 1H), 7.45 (s, 1H), 7.15-7.01 (m, 4H), 6.16 (s, 1H), 5.54 (d, J=53.5 Hz, 2H), 4.42 (s, 2H), 4.11 (d, J=31.4 Hz, 3H), 2.31 (s, 1H), 1.82 (s, 3H), 1.46 (s, 3H).

¹³C NMR (151 MHz, DMSO) δ 158.56, 154.12, 153.16, 149.67, 148.36, 146.37, 145.27, 143.19, 142.19, 138.53, 136.48, 132.49, 127.19, 123.95, 121.10, 118.56, 114.57, 108.47, 54.95, 36.26, 33.96, 31.35, 28.36, 15.64.

2. Bioactivity Assay (1) 3CL$^{pro}$ Inhibitory Activity Test

The inhibitory activity of the compounds against SARS-CoV-2 3CL$^{pro}$ was determined using fluorescence resonance energy transfer.

10 μL of the compound solutions prepared at different concentrations (final concentrations of 1000, 500, 250, 125, 62.5, 31.25, 15.63, 7.81, 3.90, 1.95 nM, in DMSO) and 40 μL of SARS-CoV-2 3CL$^{pro}$ (Shanghai Biyuntian Biotechnology Co., Ltd., final concentration: 0.5 μM, diluted with Tris-HCl buffer (20 mM Tris-HCl, 100 mM NaCl, 1 mM EDTA, pH 7.4)) were mixed, added to a black 96-well plate, incubate at 37° C. for 10 min. A reaction was initiated by adding 50 μL of the fluorescent substrate Dabcyl-KTSAVLQSGFRKME-Edans (Shanghai Biyuntian Biotechnology Co., Ltd., the final concentration: 20 μM), incubated for 10 min, and measured by a multifunctional microplate reader (Thermo Fisher Scientific Co., Ltd., Varioskan Flash) for fluorescence detection, the excitation wavelength: 340 nm, the emission wavelength: 490 nm. The fluorescence value was recorded to calculate the inhibition percentage of the sample. DMSO without compound was used as the enzyme activity control, and the Tris-HCl buffer without SARS-CoV-2 3CL$^{pro}$ was used as the blank control, and the treatment methods were the same. The IC$_{50}$ values of the samples (compounds 1-9) were calculated by nonlinear regression analysis using GraphPad Prism software.

Inhibition Rate (%)=(RFU$_{enzyme\ activity\ control}$−RFU$_{sample}$)/(RFU$_{enzyme\ activity\ control}$−RFU$_{blank\ control}$)×100%

The experimental results are shown in Tables 1 and 2 (in Table 1, the column of IC$_{50}$, A: IC50<100 nM, B: IC$_{50}$=200-500 nM, C: 500-1000 nM, D: >1000 nM), the example compounds all have inhibitory activity against 3CL$^{pro}$, among which compounds 1, 7, 12, 15, 16, 17, 18, 22 and 23 have strong inhibitory effects on 3CL$^{pro}$, with IC$_{50}$ values below 100 nM.

TABLE 1

Inhibitory activity of compounds 1-24 on 3CL$^{pro}$

| Compound Nos. | IC$_{50}$ (nM) |
|---|---|
| 1 | A |
| 2 | C |
| 3 | C |
| 4 | C |
| 5 | B |
| 6 | D |
| 7 | A |
| 8 | B |
| 9 | B |
| 10 | B |
| 11 | D |
| 12 | A |
| 13 | C |
| 14 | C |
| 15 | A |
| 16 | A |
| 17 | A |
| 18 | A |
| 19 | B |
| 20 | B |
| 21 | B |
| 22 | A |
| 23 | A |
| 24 | B |

TABLE 2

Inhibitory activity of compounds 1, 12, 17, S-217622, and PF-07321332 on 3CL$^{pro}$

| | Comp | | | | |
|---|---|---|---|---|---|
| Conc/nM | S-217622 (IC$_{50}$ = 33.02 nM) | PF-07321332 (IC$_{50}$ = 46.98 nM) | 1 (IC$_{50}$ = 92.60 nM) | 12 (IC$_{50}$ = 177.8 nM) | 17 (IC$_{50}$ = 123.2 nM) |
| 1000 | 94.01% | 89.68% | 96.17% | 88.56% | 89.73% |
| 500 | 90.80% | 73.84% | 82.46% | 68.72% | 70.62% |
| 100 | 77.55% | 60.74% | 59.34% | 37.21% | 45.44% |
| 50 | 55.62% | 56.31% | 26.24% | 21.22% | 33.16% |
| 30 | 47.83% | 43.96% | 20.83% | 16.46% | 24.39% |
| 20 | 39.52% | 41.05% | 15.20% | 12.13% | 18.22% |
| 10 | 25.77% | 26.18% | 10.92% | 8.52% | 15.16% |
| 5 | 14.64% | 12.91% | 7.62% | 5.73% | 8.20% |
| 1 | 5.02% | 4.79% | 2.35% | 2.33% | 5.00% |
| 0.1 | 0.84% | 0.59% | 1.68% | 0.76% | 0.65% |

The data in Table 1-2 showed that compounds 1-24 all had different degrees of inhibition on 3CL$^{pro}$. The IC50 values of compounds 1, 7, 12, 15, 16, 17, 18, 22 and 23 for 3CL$^{pro}$ were all less than 200 nM, indicating that the 3-triazolylmethyl-1,3,5-triazine—Inhibitory activity of 2,4-diketones against coronavirus 3CL$^{pro}$. Specifically, IC$_{50}$ of compounds 1, 12 and 17 on 3CL$^{pro}$ is, 96.60 nM, 177.8 nM, and 123.2 nM, respectively, among which compound 1 has the best inhibitory activity (IC$_{50}$<100 nM) and can be developed and applied as an anti-coronavirus drug.

(2) 3CL$^{pro}$ Cytotoxicity Test

The in vitro cytotoxicity of compounds 1, 12 and 17 was evaluated by an .MTT method. HepG2, HEK293 and A549 cells were taken in logarithmic growth phase, digested with trypsin to prepare cell suspensions. The cell density was adjusted to 5×10$^4$ cells/mL, inoculating 180 μL per well in a sterile 96-well cell culture plate, incubating for 24 h at 37° C. in a 5% CO$_2$ incubator. After the cells were attached to the bottom of the well plate, 20 μL of the drug solutions in a concentration gradient were added to each well, and 6 duplicate wells were set up in parallel, including blank group (no cells, no compounds) and control groups (no compounds). After incubating for 24 h at 37° C. in a 5% CO$_2$ constant temperature incubator, 20 μL of 5 g/L MTT solution was added to each well for 4 h. After the incubation, the culture medium in the wells was gently aspirated, 100 μL of DMSO was added to each well, and the cells were shaken at low speed for 10 min on a shaker to fully dissolve the crystals to calculate cell viability. The results are shown in Tables 3-5.

Cell viability (%)=(Sample Group GD Value−Blank Group GD Value)/(Control Group GD Value−Blank Group GD Value)

TABLE 3

The Effects of Compounds on A549 Cells
A549 cell viability

| Conc. (nM) | 400 | 200 | 100 | 50 | 25 | 12.5 | 6.25 | 3.125 | 1.5625 |
|---|---|---|---|---|---|---|---|---|---|
| PF-07321332 | 92.31% | 93.74% | 95.91% | 95.76% | 93.21% | 94.43% | 94.77% | 96.01% | 98.28% |
| S-217622 | 91.09% | 94.62% | 95.46% | 96.92% | 96.09% | 96.81% | 97.39% | 97.96% | 98.63% |
| 1 | 93.02% | 95.01% | 98.69% | 98.76% | 98.71% | 98.93% | 98.82% | 98.65% | 99.46% |
| 12 | 90.13% | 94.13% | 96.61% | 98.03% | 96.21% | 97.32% | 96.55% | 97.34% | 98.52% |
| 17 | 90.01% | 93.31% | 97.73% | 97.03% | 97.38% | 97.61% | 97.13% | 97.39% | 98.63% |

TABLE 4

The Effects of Compounds on HEK293 Cells
HEK293 cell viability

| Conc. (nM) | 400 | 200 | 100 | 50 | 25 | 12.5 | 6.25 | 3.125 | 1.5625 |
|---|---|---|---|---|---|---|---|---|---|
| PF-07321332 | 80.26% | 81.64% | 80.62% | 85.81% | 86.22% | 89.70% | 90.14% | 92.68% | 92.10% |
| S-217622 | 80.71% | 80.75% | 81.65% | 87.90% | 87.99% | 90.14% | 90.77% | 91.12% | 93.54% |
| 1 | 81.17% | 83.54% | 84.87% | 88.49% | 86.03% | 89.50% | 94.02% | 96.70% | 99.03% |
| 12 | 78.23% | 80.57% | 81.24% | 82.91% | 84.22% | 90.69% | 92.31% | 93.03% | 93.67% |
| 17 | 75.31% | 81.72% | 83.33% | 84.35% | 83.11% | 90.64% | 92.03% | 93.56% | 93.36% |

TABLE 5

The Effects of Compounds on HepG2 Cells
HEPG2 cell viability

| Conc. (nM) | 400 | 200 | 100 | 50 | 25 | 12.5 | 6.25 | 3.125 | 1.5625 |
|---|---|---|---|---|---|---|---|---|---|
| PF-07321332 | 81.61% | 83.06% | 83.22% | 84.71% | 84.94% | 85.17% | 93.86% | 94.29% | 95.60% |
| S-217622 | 79.89% | 83.68% | 84.16% | 87.29% | 87.94% | 90.01% | 92.69% | 94.49% | 95.19% |
| 1 | 82.62% | 85.58% | 87.72% | 88.09% | 90.35% | 95.39% | 97.83% | 96.29% | 97.09% |
| 12 | 76.67% | 81.38% | 86.63% | 86.83% | 88.36% | 90.22% | 93.31% | 95.07% | 95.73% |
| 17 | 77.31% | 80.72% | 84.08% | 86.24% | 90.31% | 91.76% | 94.04% | 95.63% | 95.86% |

Table 3-5 shows the inhibition rates of PF-07321332, S-217622, and representative compounds 1, 12 and 17 on A549 cells, HEK293 and HepG2 cells at different concentrations, respectively. The data show that the inhibitory rate of compound 1 on A549 cells, HepG2 cells and HEK293 cells was lower than that of PF-07321332 and S-217622 at any concentration. For compound 12 and compound 17 at 400 nM and 200 nM on the three cells tested, the toxicity was slightly higher than that of PF-07321332 and S-217622, but when A549 cells, HEK293 and HepG2 cells were treated at 12.5 nM and lower, the cell viability was higher than that of PF-07321332 and S-217622. In summary, compound 1 has the characteristics of good inhibitory activity and low toxicity to 3CL protease, and can be further studied.

The above content is only to illustrate the technical idea of the present invention, and cannot limit the protection scope of the present invention. Any modification made on the basis of the technical solution proposed in accordance with the technical idea of the present invention falls within the scope of the claims of the present invention.

The invention claimed is:

1. A compound of formula I, a pharmaceutically acceptable salt, or a tautomer thereof:

formula I

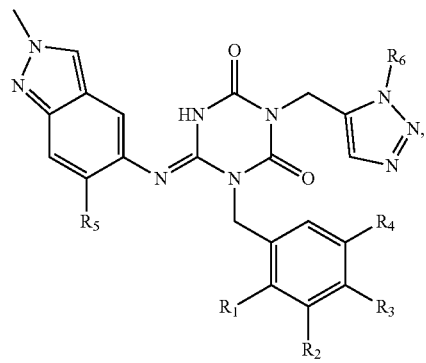

wherein $R_1$, $R_2$, $R_3$ and $R_4$ are independently selected from the group consisting of hydrogen, methyl, tert-butyl, methoxy, difluoromethyl, trifluoromethyl, trifluoromethoxy, nitro, halogen, phenyl and aromatic heterocyclic; $R_5$ is a hydrogen or halogen; and $R_6$ is hydrogen, C1-4 alkyl or C1-4 cycloalkyl.

2. The compound of claim 1, wherein the compound is selected from the group consisting of:

1
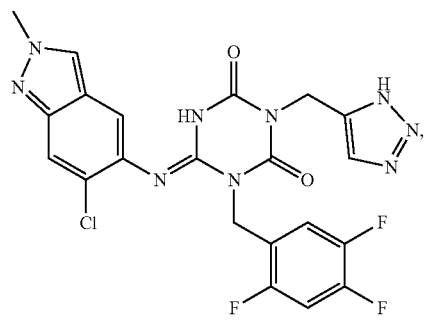

2
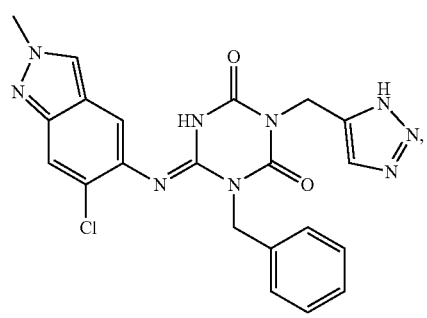

3
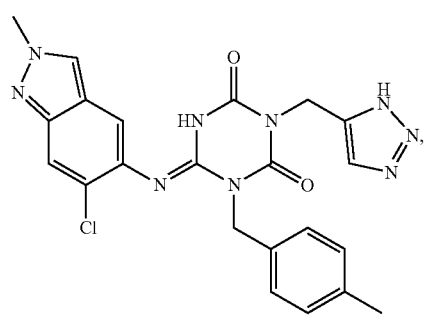

4
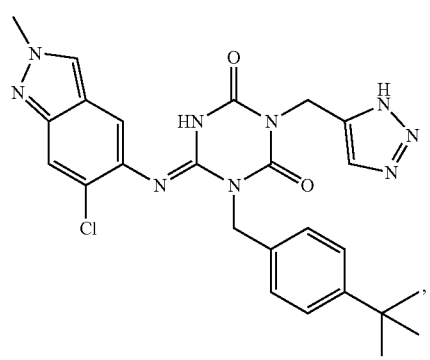

5
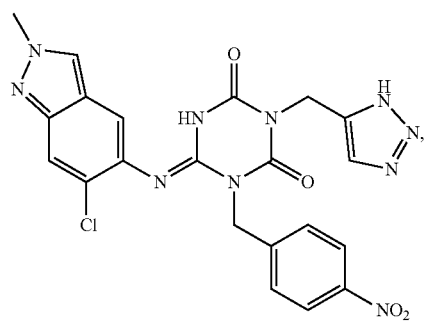

6
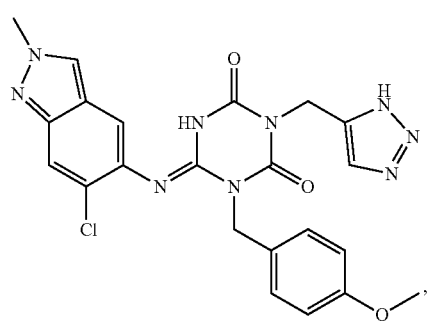

7
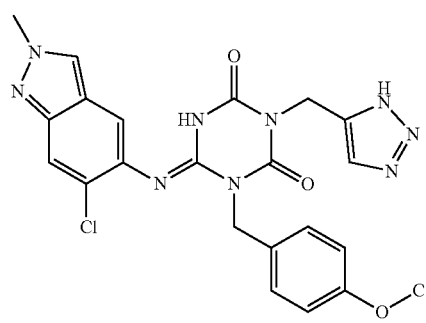

8
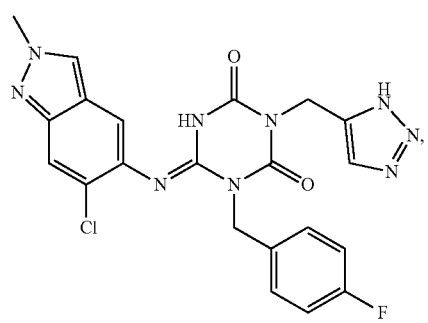

9
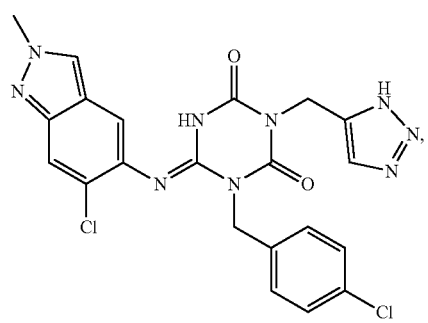

10
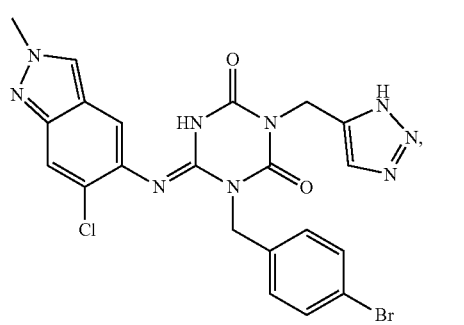
11
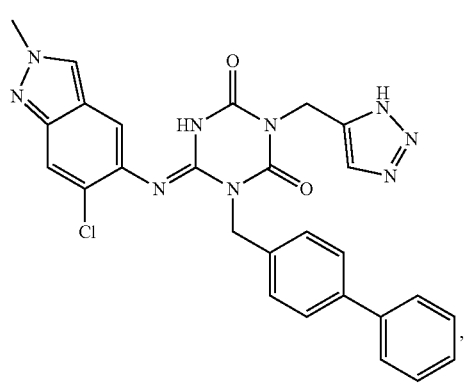
12
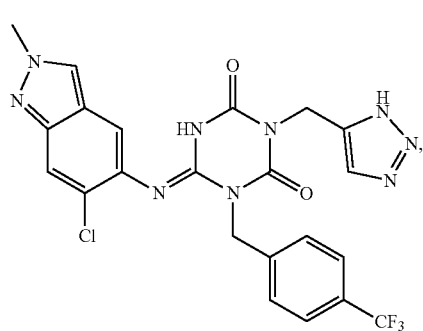
13
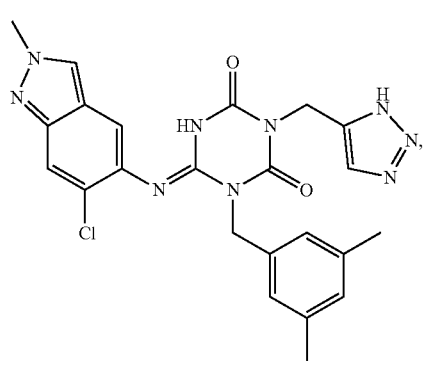
14
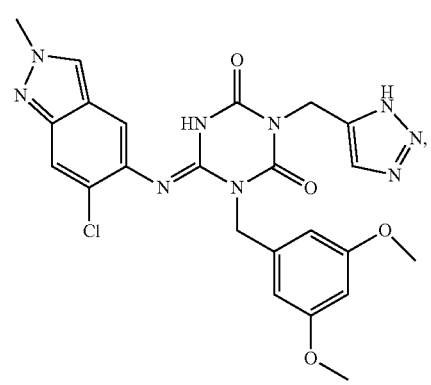
15
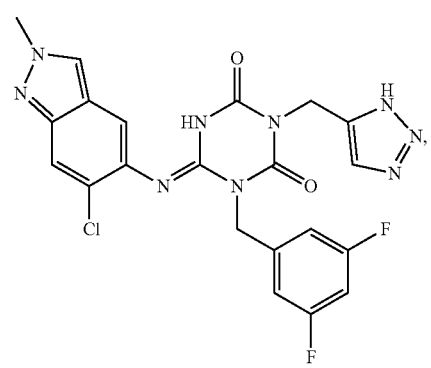
16
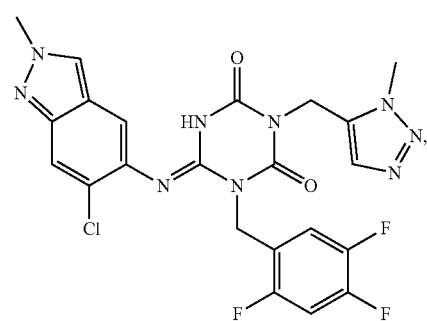
17
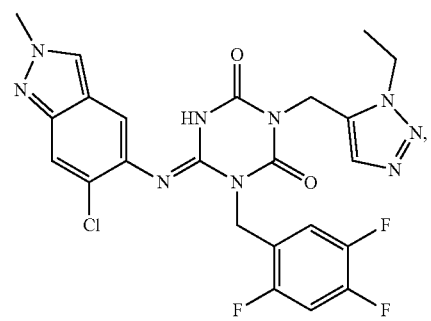

-continued
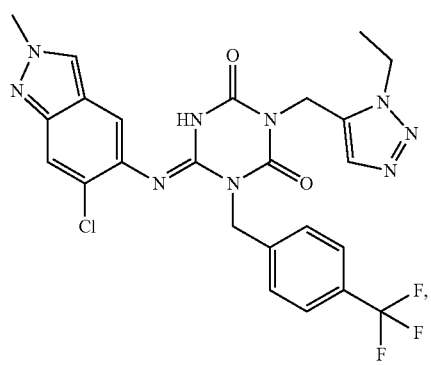
18
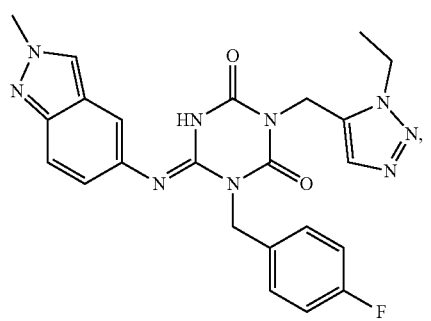
19
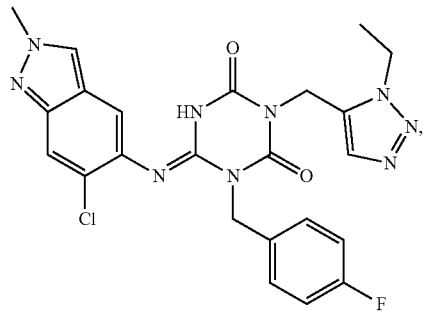
20
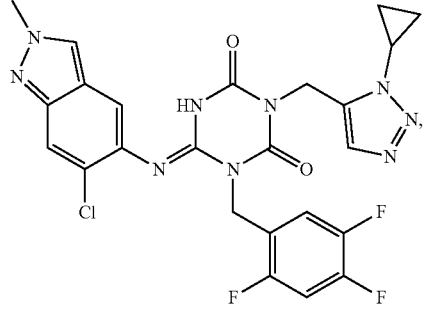
21
-continued
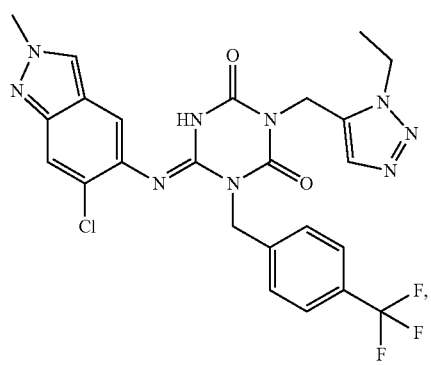
22
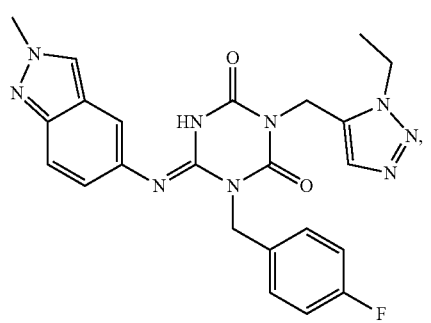
23
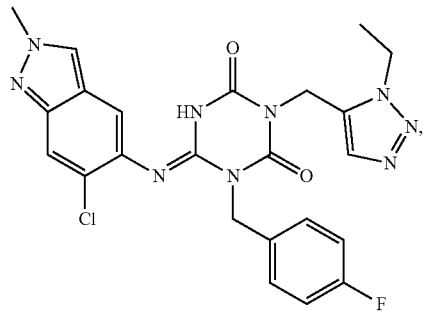
24
* * * * *